(12) United States Patent
Conte et al.

(10) Patent No.: US 8,497,288 B2
(45) Date of Patent: Jul. 30, 2013

(54) HEXAHYDROPYRROLOIMIDAZOLONE COMPOUNDS

(75) Inventors: Aurelia Conte, Shanghai (CN); Daniel Hunziker, Moehlin (CH); Werner Neidhart, Hagenthal-le-Bas (FR); Matthias Nettekoven, Grenzach-Wyhlen (DE); Tanja Schulz-Gasch, Ziefen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/461,835

(22) Filed: May 2, 2012

(65) Prior Publication Data
US 2012/0289549 A1    Nov. 15, 2012

(30) Foreign Application Priority Data
May 9, 2011   (EP) ..................... 11165232

(51) Int. Cl.
*A61K 31/4188* (2006.01)
*A61K 31/4439* (2006.01)
*C07D 401/02* (2006.01)

(52) U.S. Cl.
USPC .................... 514/338; 514/387; 546/273.1

(58) Field of Classification Search
None
See application file for complete search history.

(56) References Cited

U.S. PATENT DOCUMENTS
2004/0019063 A1* 1/2004 Sun et al. ............. 514/259.1

FOREIGN PATENT DOCUMENTS
WO   2010/02876    3/2010
WO   2010/130665   11/2010

OTHER PUBLICATIONS
(International Search Report PCT/EP2012/058173 Jul. 27, 2012).

* cited by examiner

*Primary Examiner* — Michael Barker
*Assistant Examiner* — Ana Z Muresan

(57) ABSTRACT

The invention provides novel compounds having the general formula (I),

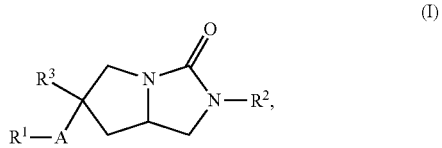

wherein $R^1$, $R^2$, $R^3$ and A are as described herein, compositions including the compounds and methods of using the compounds. These compounds are useful as inhibitors of hormone sensitive lipase (HSL) and may be used in the treatment of diabetes, metabolic syndrome, dyslipidemia, atherosclerosis, obesity, cardiovascular diseases, myocardial dysfunction, inflammation, non-alcoholic fatty liver disease and non-alcoholic steatohepatitis.

33 Claims, No Drawings

HEXAHYDROPYRROLOIMIDAZOLONE COMPOUNDS

PRIORITY TO RELATED APPLICATION(S)

This application claims the benefit of European Patent Application No. 11165232.7, filed May 9, 2011, which is hereby incorporated by reference in its entirety.

FIELD OF THE INVENTION

The present invention relates to organic compounds useful for therapy or prophylaxis in a mammal. In particular, the compounds of the present invention are useful as inhibitors of hormone sensitive lipase (HSL) and may be used in the treatment of diabetes, metabolic syndrome, dyslipidemia, atherosclerosis, obesity, cardiovascular diseases, myocardial dysfunction, inflammation, non-alcoholic fatty liver disease and non-alcoholic steatohepatitis.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess. The release of free fatty acids (FFA) from TAG is stimulated by catecholamines and regulated by hormones such as insulin, glucagon and epinephrine. The most important enzyme in WAT believed responsible for hormone regulated hydrolysis of triglyceride is hormone sensitive lipase (HSL).

Dysregulation of adipocyte lipolysis, resulting in elevated circulating non-esterified fatty acids (NEFA) is associated with obesity and co-morbidities including the development of type 2 diabetes. Obese or insulin resistant subjects have increased visceral adipose tissue depots. These depots contain elevated levels of HSL protein and exhibit enhanced lipolytic activity as they are resistant to the insulin-mediated suppression of lipolysis. This results in increased plasma levels of free fatty acids (FFA), which further exacerbates insulin resistance due to the accumulation of triglycerides in tissues other than WAT such as liver, pancreas and muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

Elevated FFAs are also associated with increased cardiovascular risk, including atherosclerosis and myocardial dysfunction. Furthermore, high lipolytic activity and elevated FFAs lead to increased insulin resistance and hypertension in hypertensive rats. The FFA collect in the liver and lead to increased production of TAG, which are packaged into very low density lipoproteins (VLDL) which are secreted. Therefore, reducing the activity of HSL would decrease the release of FFA to the blood, thus limiting the supply of FFA to the liver for TAG synthesis. Thus, HSL inhibitors could have beneficial effects as treatment of non-alcoholic fatty liver disease (NAFLD) and non-alcoholic steatohepatitis (NASH).

SUMMARY OF THE INVENTION

The present invention relates to compounds according to formula (I),

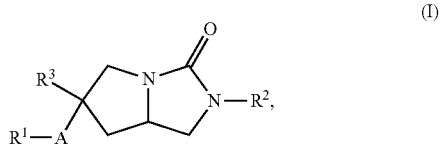

wherein $R^1$ is selected from the group consisting of: alkyl, haloalkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, heteroaryl, substituted heteroaryl, heteroarylalkyl and substituted heteroarylalkyl; wherein said substituted phenyl, substituted phenylalkyl, substituted phenoxyalkyl, substituted heteroaryl and substituted heteroarylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^2$ is selected from the group consisting of: phenyl, substituted phenyl, heteroaryl and substituted heteroaryl, wherein said substituted phenyl and substituted heteroaryl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^3$ is selected from the group consisting of: hydrogen, hydroxy and alkoxy, wherein, when $R^3$ is hydroxy or alkoxy, A is a bond;

$R^4$ is selected from the group consisting of: hydrogen, alkyl and cycloalkyl;

$R^5$ is selected from the group consisting of: hydrogen, alkyl and cycloalkyl; and A is selected from the group consisting of: —O—, —OC(O)—, —NR$^4$C(O)O—, —NR$^4$—, —C(O)NR$^4$—, —NR$^4$C(O)NR$^5$—, —S(O)$_2$NR$^4$—, —NR$^4$S(O)NR$^5$—, —NR$^4$S(O)$_2$ NR$^5$—, —S—, —S(O)—, —S(O)$_2$— and a bond, wherein, when A is a bond, $R^1$ is alkoxyalkyl or haloalkoxyalkyl.

The present invention also relates to pharmaceutically acceptable salts and esters of the aforementioned compounds.

Further aspects of the present invention include the use of compounds of formula (I) and their aforementioned salts and esters as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis and the use of the said compounds, salts or esters for the production of medicaments for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxymethyl, ethoxyethyl, methoxypropyl, ethoxypropyl, n-butoxymethyl and terbutoxymethyl. Particular alkoxyalkyl group include ethoxymethyl, n-butoxymethyl and terbutoxymethyl.

The term "alkoxyhaloalkyl" denotes an alkyl wherein at least one of the hydrogen atoms of the alkyl has been replaced by an alkoxy group and wherein at least one of the hydrogen atoms of the alkyl has been replaced by a halogen. Examples of alkoxyhaloalkyl include methoxytrifluoroethyl or methoxytrifluoropropyl.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, n-propyl, isopropyl, dimethylpropyl, n-butyl, iso-butyl, sec-butyl, tert-butyl, methylbutyl and dimethylbutyl. Particular alkyl groups include methyl, n-propyl, dimethylpropyl, iso-butyl, sec-butyl, methylbutyl and dimethylbutyl. More particular alkyl group is methyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "haloalkoxy" denotes an alkoxy group wherein at least one of the hydrogen atoms of the alkoxy group has been replaced by same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and trifluoroethoxy. More particular haloalkoxy group is trifluoromethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl group is 2,2,2-trifluoroethoxymethyl.

The term "haloalkyl" denotes an alkyl group wherein at least one of the hydrogen atoms of the alkyl group has been replaced by same or different halogen atoms. Examples of haloalkyl include fluoromethyl, difluoromethyl, trifluoromethyl, trifluoroethyl, trifluoromethylethyl and pentafluoroethyl. A particular haloalkyl groups is trifluoromethyl.

The term "halogen" and "halo" are used interchangeably herein and denote fluoro, chloro, bromo, or iodo. Particular halogens are chloro and fluoro. More particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl group is pyridinyl.

The term "heteroarylalkyl" denotes an alkyl group wherein at least one of the hydrogen atoms of the alkyl group has been replaced by a heteroaryl group. Examples of heteroarylalkyl is pyridinylalkyl.

The term "hydroxy" denotes a —OH group.

The term "hydroxyhaloalkyl" denotes an alkyl wherein at least one of the hydrogen atoms of the alkyl has been replaced by a hydroxy group and wherein at least one of the hydrogen atoms of the alkyl has been replaced by a halogen. Examples of hydroxyhaloalkyl include hydroxytrifluoroethyl, hydroxytrifluoropropyl and hydroxyhexafluoropropyl.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "phenoxy" denotes a group of the formula —O—R', wherein R' is a phenyl.

The term "phenoxyalkyl" denotes an alkyl group wherein at least one of the hydrogen atoms of the alkyl group has been replaced by a phenoxy group. Exemplary phenoxyalkyl groups include phenoxymethyl, phenoxyethyl and phenoxypropyl. Particular alkoxyalkyl group is phenoxymethyl.

The term "phenylalkyl" denotes an alkyl group wherein at least one of the hydrogen atoms of the alkyl group has been replaced by a phenyl. Examples of phenylalkyl include phenylmethyl, phenylethyl, phenylpropyl and phenylmethylpropyl. Particular phenylalkyl groups are phenylmethyl and phenylethyl.

The present invention relates to a compound according to formula (I),

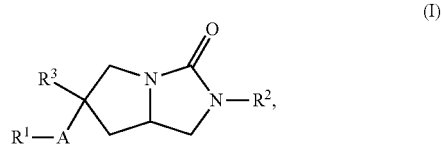

wherein
R¹ is selected from the group consisting of: alkyl, haloalkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, heteroaryl, substituted heteroaryl, heteroarylalkyl and substituted heteroarylalkyl; wherein said substituted phenyl, substituted phenylalkyl, substituted phenoxyalkyl, substituted heteroaryl and substituted heteroarylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^2$ is selected from the group consisting of: phenyl, substituted phenyl, heteroaryl and substituted heteroaryl, wherein said substituted phenyl and substituted heteroaryl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

$R^3$ is selected from the group consisting of: hydrogen, hydroxy and alkoxy, wherein, when $R^3$ is hydroxy or alkoxy, A is a bond;

$R^4$ is selected from the group consisting of: hydrogen, alkyl and cycloalkyl;

$R^5$ is selected from the group consisting of: hydrogen, alkyl and cycloalkyl; and A is selected from the group consisting of: —O—, —OC(O)—, —NR$^4$C(O)O—, —NR$^4$—, —C(O)NR$^4$—, —NR$^4$C(O)NR$^5$—, —S(O)$_2$NR$^4$—, —NR$^4$S(O)NR$^5$—, —NR$^4$S(O)$_2$ NR$^5$—, —S—, —S(O)—, —S(O)$_2$— and a bond, wherein, when A is a bond, $R^1$ is alkoxyalkyl or haloalkoxyalkyl.

The present invention also relates to a pharmaceutically acceptable salt of such a compound.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are trimethylsilyl (TMS), triethylsilyl (TES), triisopropylilyl (TIPS), terbutyldimethylsilyl (TBS) and tertbutyldiphenylsilyl (TBDPS). Further particular protecting group is the tertbutyldiphenylsilyl (TBDPS).

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts thereof.

A further embodiment of the present invention are compounds according to formula (I) as described herein, wherein $R^1$ is selected from the group consisting of: alkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, pyridinyl, substituted pyridinyl, pyridinylalkyl and substituted pyridinylalkyl; wherein said substituted phenyl, substituted phenylalkyl, substituted phenoxyalkyl, substituted pyridinyl and substituted pyridinylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl.

A particular embodiment of the present invention are compounds according to formula (I) as described herein, wherein $R^1$ is selected from the group consisting of: alkyl, alkoxyalkyl, haloalkoxyalkyl, hydroxyalkyl, substituted phenyl, phenylalkyl, substituted phenylalkyl, phenoxyalkyl and substituted pyridinyl; wherein said substituted phenyl, substituted phenylalkyl and substituted pyridinyl are substituted with one to three substituents independently selected from the group consisting of alkyl, halogen and hydroxy.

In a further embodiment of the present invention are compounds according to formula (I) as described herein, wherein $R^1$ is haloalkoxyalkyl or phenyl substituted with one halogen.

Another further embodiment of the present invention are compounds according to formula (I) as described herein, wherein $R^1$ is haloalkoxyalkyl.

A particular embodiment of the present invention are compounds according to formula (I) as described herein, wherein $R^1$ is 2,2,2-trifluoroethoxymethyl.

A further particular embodiment of the present invention are compounds according to formula (I) as described herein, wherein $R^1$ is phenyl substituted with one halogen.

Also an embodiment of the present invention are compounds according to formula (I) as described herein, wherein $R^1$ is selected from the group consisting of: 2-chlorophenyl, 2-fluorophenyl, 3-fluorophenyl and 4-chlorophenyl.

Another embodiment of the present invention are compounds according to formula (I) as described herein, wherein $R^2$ is phenyl substituted with one haloalkoxy.

The present invention also relates to compounds according to formula (I) as described herein, wherein $R^2$ is phenyl substituted with one substituent selected from trifluoromethoxy and 2,2,2-trifluoroethoxy.

A further particular embodiment of the present invention are compounds according to formula (I) as described herein, wherein R² is 4-trifluoromethoxyphenyl or 4-(2,2,2-trifluoroethoxy)phenyl.

A more particular embodiment of the present invention are compounds according to formula (I) as described herein, wherein R² is 4-trifluoromethoxyphenyl.

Also an embodiment of the present invention are compounds according to formula (I) as described herein, wherein R³ is hydrogen or hydroxy, wherein, when R³ is hydroxy, A is a bond.

The present invention also relates to compounds according to formula (I) as described herein, wherein R³ is hydrogen.

Another embodiment of the present invention are compounds according to formula (I) as described herein, wherein R³ is hydroxy and A is a bond.

A further particular embodiment of the present invention are compounds according to formula (I) as described herein, wherein R⁴ is hydrogen or alkyl.

A particular embodiment of the present invention are compounds according to formula (I) as described herein, wherein R⁴ is hydrogen.

Also an embodiment of the present invention are compounds according to formula (I) as described herein, wherein R⁴ is alkyl.

Also an embodiment of the present invention are compounds according to formula (I) as described herein, wherein R⁵ is hydrogen.

Another embodiment of the present invention are compounds according to formula (I) as described herein, wherein A is selected from the group consisting of: —O—, —NR⁴C(O)O—, —C(O)NR⁴—, —NR⁴C(O)NR⁵—, —S(O)₂NR⁴—, —S(O)₂— and a bond, wherein, when A is a bond, R¹ is alkoxyalkyl or haloalkoxyalkyl.

The present invention also relates to compounds according to formula (I) as described herein, wherein A is a bond and R¹ is alkoxyalkyl or haloalkoxyalkyl.

Also an embodiment of the present invention are compounds according to formula (I) as described herein, wherein R¹ and A together form R¹—O—, R¹—NR⁴C(O)O—, R¹—C(O)NR⁴—, R¹—NR⁴C(O)NR⁵—, R¹—S(O)₂NR⁴— or R¹—S(O)₂—.

Another embodiment of the present invention are compounds according to formula (I) as described herein, wherein A is —S(O)₂NR⁴—.

Also an embodiment of the present invention are compounds according to formula (I) as described herein, wherein A is —O—.

Also an embodiment of the present invention are compounds according to formula (I) as described herein, wherein A is —C(O)NR⁴—.

A particular embodiment of the present invention are compounds according to formula (I) as described herein, wherein A is —NR⁴C(O)NR⁵—.

A further embodiment of the present invention are compounds according to formula (I) as described herein of formula (Ia)

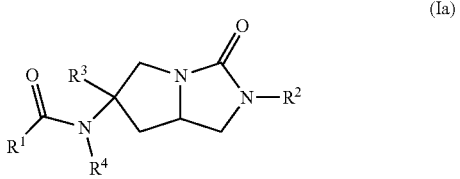

(Ia)

Also a further embodiment of the present invention are compounds according to formula (I) as described herein of formula (Ib)

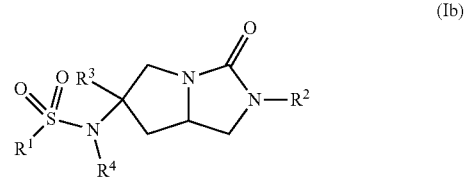

(Ib)

Particular examples of compounds of formula (I) as described herein are selected from the group consisting of:

2-Chloro-N-[(6R,7aS)-3-oxo-2-(4-trifluoromethoxy-phenyl)-hexahydro-pyrrolo[1,2-c]imidazol-6-yl]-benzamide;

2-Chloro-N-[(6R,7aS)-3-oxo-2-(4-trifluoromethoxy-phenyl)-hexahydro-pyrrolo[1,2-c]imidazol-6-yl]-benzenesulfonamide;

(6R,7aS)-6-(Toluene-4-sulfonyl)-2-(4-trifluoromethoxy-phenyl)-hexahydro-pyrrolo[1,2-c]imidazol-3-one;

(6R,7aS)-6-(3-Methyl-butane-1-sulfonyl)-2-(4-trifluoromethoxy-phenyl)-hexahydro-pyrrolo[1,2-c]imidazol-3-one;

(6R,7aS)-6-(4-Fluoro-benzenesulfonyl)-2-(4-trifluoromethoxy-phenyl)-hexahydro-pyrrolo[1,2-c]imidazol-3-one;

(6R,7aS)-6-(1-Phenyl-ethoxy)-2-(4-trifluoromethoxy-phenyl)-hexahydro-pyrrolo[1,2-c]imidazol-3-one;

Propyl-carbamic acid (6R,7aS)-3-oxo-2-(4-trifluoromethoxy-phenyl)-hexahydro-pyrrolo[1,2-c]imidazol-6-yl ester;

(4-Fluoro-benzyl)-carbamic acid (6R,7aS)-3-oxo-2-(4-trifluoromethoxy-phenyl)-hexahydro-pyrrolo[1,2-c]imidazol-6-yl ester;

N-[(6R,7aS)-3-Oxo-2-(4-trifluoromethoxy-phenyl)-hexahydro-pyrrolo[1,2-c]imidazol-6-yl]-C-phenyl-methanesulfonamide;

4-Methyl-N-[(6R,7aS)-3-oxo-2-(4-trifluoromethoxy-phenyl)-hexahydro-pyrrolo[1,2-c]imidazol-6-yl]-benzenesulfonamide;

2-Methyl-propane-1-sulfonic acid [(6R,7aS)-3-oxo-2-(4-trifluoromethoxy-phenyl)-hexahydro-pyrrolo[1,2-c]imidazol-6-yl]-amide;

3-Chloro-N-[(6R,7aS)-3-oxo-2-(4-trifluoromethoxy-phenyl)-hexahydro-pyrrolo[1,2-c]imidazol-6-yl]-benzenesulfonamide;

4-Chloro-N-[(6R,7aS)-3-oxo-2-(4-trifluoromethoxy-phenyl)-hexahydro-pyrrolo[1,2-c]imidazol-6-yl]-benzenesulfonamide;

2-Fluoro-N-[(6R,7aS)-3-oxo-2-(4-trifluoromethoxy-phenyl)-hexahydro-pyrrolo[1,2-c]imidazol-6-yl]-benzenesulfonamide;

2-Chloro-pyridine-3-sulfonic acid [(6R,7aS)-3-oxo-2-(4-trifluoromethoxy-phenyl)-hexahydro-pyrrolo[1,2-c]imidazol-6-yl]-amide;

2-Hydroxy-pyridine-3-sulfonic acid [(6R,7aS)-3-oxo-2-(4-trifluoromethoxy-phenyl)-hexahydro-pyrrolo[1,2-c]imidazol-6-yl]-amide;

1-Methyl-3-[(6R,7aS)-3-oxo-2-(4-trifluoromethoxy-phenyl)-hexahydro-pyrrolo[1,2-c]imidazol-6-yl]-1-propyl-urea;

1-(3-Fluoro-phenyl)-1-methyl-3-[(6R,7aS)-3-oxo-2-(4-trifluoromethoxy-phenyl)-hexahydro-pyrrolo[1,2-c]imidazol-6-yl]-urea;

3-Chloro-N-[(6R,7aS)-3-oxo-2-(4-trifluoromethoxy-phenyl)-hexahydro-pyrrolo[1,2-c]imidazol-6-yl]-benzamide;

4-Methyl-N-[(6S,7aS)-3-oxo-2-(4-trifluoromethoxy-phenyl)-hexahydro-pyrrolo[1,2-c]imidazol-6-yl]-benzenesulfonamide;

4-Chloro-N-[(6R,7aS)-3-oxo-2-(4-trifluoromethoxy-phenyl)-hexahydro-pyrrolo[1,2-c]imidazol-6-yl]-benzamide;
2-Fluoro-N-[(6R,7aS)-3-oxo-2-(4-trifluoromethoxy-phenyl)-hexahydro-pyrrolo[1,2-c]imidazol-6-yl]-benzamide;
4-Chloro-N-[(6S,7aS)-3-oxo-2-(4-trifluoromethoxy-phenyl)-hexahydro-pyrrolo[1,2-c]imidazol-6-yl]-benzenesulfonamide;
3,3-Dimethyl-N-[(6R,7aS)-3-oxo-2-(4-trifluoromethoxy-phenyl)-hexahydro-pyrrolo[1,2-c]imidazol-6-yl]-butyramide;
2-Chloro-pyridine-3-sulfonic acid [(6S,7aS)-3-oxo-2-(4-trifluoromethoxy-phenyl)-hexahydro-pyrrolo[1,2-c]imidazol-6-yl]-amide;
N-[(6R,7aS)-3-Oxo-2-(4-trifluoromethoxy-phenyl)-hexahydro-pyrrolo[1,2-c]imidazol-6-yl]-2-phenoxy-acetamide;
2-tert-Butoxy-N-[(6R,7aS)-3-oxo-2-(4-trifluoromethoxy-phenyl)-hexahydro-pyrrolo[1,2-c]imidazol-6-yl]-acetamide;
3-Chloro-N-[(6S,7aS)-3-oxo-2-(4-trifluoromethoxy-phenyl)-hexahydro-pyrrolo[1,2-c]imidazol-6-yl]-benzenesulfonamide;
2-Fluoro-N-[(6S,7aS)-3-oxo-2-(4-trifluoromethoxy-phenyl)-hexahydro-pyrrolo[1,2-c]imidazol-6-yl]-benzenesulfonamide;
2-Methyl-propane-1-sulfonic acid [(6S,7aS)-3-oxo-2-(4-trifluoromethoxy-phenyl)-hexahydro-pyrrolo[1,2-c]imidazol-6-yl]-amide;
N-[(6S,7aS)-3-Oxo-2-(4-trifluoromethoxy-phenyl)-hexahydro-pyrrolo[1,2-c]imidazol-6-yl]-C-phenyl-methanesulfonamide;
(6R,7aS)-6-(2-Hydroxy-pentyloxy)-2-(4-trifluoromethoxy-phenyl)-hexahydro-pyrrolo[1,2-c]imidazol-3-one;
(6S,7aR)-6-(3-Methyl-butoxy)-2-[4-(2,2,2-trifluoro-ethoxy)-phenyl]-hexahydro-pyrrolo[1,2-c]imidazol-3-one;
(6S,7aR)-6-Isobutoxy-2-[4-(2,2,2-trifluoro-ethoxy)-phenyl]-hexahydro-pyrrolo[1,2-c]imidazol-3-one;
2-Chloro-N-{(6R,7aR)-3-oxo-2-[4-(2,2,2-trifluoro-ethoxy)-phenyl]-hexahydro-pyrrolo[1,2-c]imidazol-6-yl}-benzenesulfonamide;
(6R,7aR)-6-(3-Methyl-butoxy)-2-[4-(2,2,2-trifluoro-ethoxy)-phenyl]-hexahydro-pyrrolo[1,2-c]imidazol-3-one;
2-Chloro-N-{(6R,7aR)-3-oxo-2-[4-(2,2,2-trifluoro-ethoxy)-phenyl]-hexahydro-pyrrolo[1,2-c]imidazol-6-yl}-benzenesulfonamide;
(6S,7aS)-6-Butoxymethyl-6-hydroxy-2-[4-(2,2,2-trifluoro-ethoxy)-phenyl]-hexahydro-pyrrolo[1,2-c]imidazol-3-one;
(6S,7aS)-6-Ethoxymethyl-6-hydroxy-2-[4-(2,2,2-trifluoro-ethoxy)-phenyl]-hexahydro-pyrrolo[1,2-c]imidazol-3-one;
(6S,7aS)-6-Hydroxy-6-(2,2,2-trifluoro-ethoxymethyl)-2-[4-(2,2,2-trifluoro-ethoxy)-phenyl]-hexahydro-pyrrolo[1,2-c]imidazol-3-one;
and pharmaceutically acceptable salts thereof.

Further particular examples of compounds of formula (I) as described herein are selected from the group consisting of:
2-Chloro-N-[(6R,7aS)-3-oxo-2-(4-trifluoromethoxy-phenyl)-hexahydro-pyrrolo[1,2-c]imidazol-6-yl]-benzenesulfonamide;
2-Fluoro-N-[(6R,7aS)-3-oxo-2-(4-trifluoromethoxy-phenyl)-hexahydro-pyrrolo[1,2-c]imidazol-6-yl]-benzenesulfonamide;
1-(3-Fluoro-phenyl)-1-methyl-3-[(6R,7aS)-3-oxo-2-(4-trifluoromethoxy-phenyl)-hexahydro-pyrrolo[1,2-c]imidazol-6-yl]-urea;
4-Chloro-N-[(6R,7aS)-3-oxo-2-(4-trifluoromethoxy-phenyl)-hexahydro-pyrrolo[1,2-c]imidazol-6-yl]-benzamide;
(6S,7aS)-6-Hydroxy-6-(2,2,2-trifluoro-ethoxymethyl)-2-[4-(2,2,2-trifluoro-ethoxy)-phenyl]-hexahydro-pyrrolo[1,2-c]imidazol-3-one;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In more detail, the compounds of formula I can be manufactured by the methods given below, by the methods given in the examples or by analogous methods. Appropriate reaction conditions for the individual reaction steps are known to a person skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

Compounds of formula (I) are readily accessible as outlined in scheme 1 and 2.

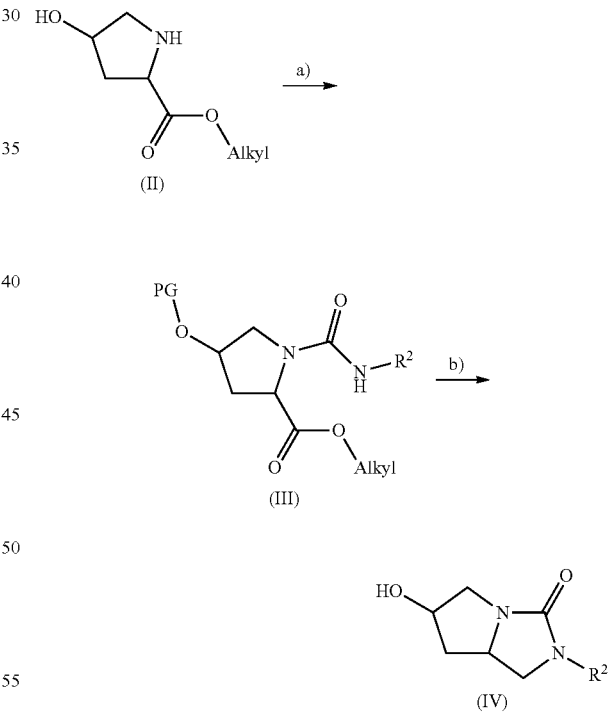

Scheme 1

PG is protecting group
Alkyl is e.g. methyl or ethyl
a) Hydroxy-proline derivatives (II) are either commercially available or can be synthesized according to methods known in the art. These proline derivatives are conveniently reacted with isocyanates with a base such as NEt₃, DIPEA and the like. Subsequently the free hydroxyl-group is protected with a suitable protecting group e.g. TBDPS and the like to afford proline derivatives (III).
b) Proline derivatives (III) are conveniently reduced with a suitable reducing agent such as NaBH₄, LiBH₄ and the like, to access the free alcohol which is conveniently cyclised through conversion of the free hydroxyl group to a leaving group such as mesylate, tosylate or halogen derivatives to access protected pyrrolo-imidazole derivatives which are conveniently deprotected under suitable conditions such as TBAF, NF and the like to access derivatives (IV).

Scheme 2

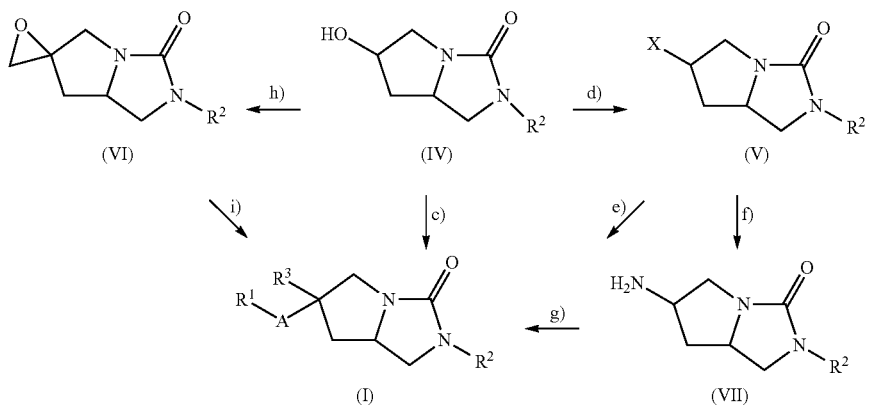

c) Direct conversion of (IV) to final derivatives (I), wherein R³ is hydrogen, can conveniently be done through nucleophilic substitution with suitable electrophiles using method known to the man skilled in the art.
d) Conversion of the free OH functionality in (IV) to a suitable leaving group such as X is halogen, particularly bromine using e.g triphenylphosphine and tetrabromomethane in THF, leads to compounds of formula (V).
e) Subsequent reaction of (V) with a nucleophile in the presence of a base yields final compounds (I), wherein R³ is hydrogen.
f) Compounds of formula (V) can be converted in compounds of formula (VII) by first reacting the compounds of formula (V) with e.g. sodium azide in DMF. The reduction by e.g hydrogenation of the so-obtained azide derivatives leads to compounds of formula (VII)
g) Subsequent reaction of (VII) with a nucleophile leads to final compounds (I), wherein R³ is hydrogen and A is —NR⁴C(O)O—, —NR⁴—, —C(O)NR⁴—, —NR⁴C(O)NR⁵—, —S(O)₂NR⁴—, —NR⁴S(O)NR⁵— or —NR⁴S(O)₂NR⁵—.
h) Conversion of the free OH functionality in (IV) to the respective ketone can be achieved with various oxidising agents such as PDC and the like and subsequent conversion to the epoxide (VI) can be done with trimethyl sulfoxonium iodide, NaH in DMSO.
i) Opening of the epoxide (VI) can be done with various nucleophiles optionally in the presence of a base to yield final compounds (I).

Compounds of formula (I), wherein, A is —S(O)— or —S(O)₂— can be obtained by oxidation of corresponding compounds of formula (I), wherein A is —S— by method known to the man skilled in the art.

Also an embodiment of the present invention is a process to prepare a compound of formula (I) as defined above comprising the reaction of a) a compound of formula (IV);

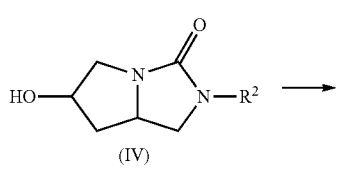

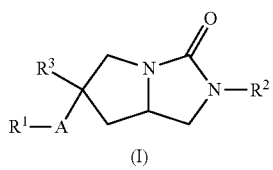

In particular in presence or not of a base, particularly sodium hydride and potassium tert-butoxide, in a solvent, particularly DMF and THF, at a temperature comprised between RT and reflux, wherein R¹, R² and R³ are as defined herein and A is —O—, —OC(O)— or —NR⁴C(O)O—.
or
b) a compound of formula (VII);

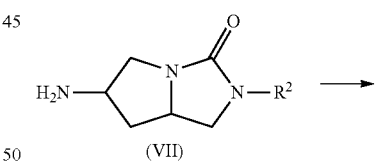

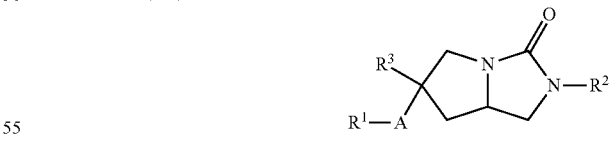

In particular in presence or not of a base, particularly diispropoylethylamine and triethylamine, in a solvent, particularly CH₂Cl₂, at a temperature comprised between RT and reflux, wherein R¹, R² and R³ are as defined herein and A is —NR⁴C(O)O—, —NR⁴—, —C(O)NR⁴—, —NR⁴C(O)NR⁵—, —S(O)₂NR⁴—, —NR⁴S(O)NR⁵— or —NR⁴S(O)₂NR⁵—.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

Also an object of the present invention is the use of a compound according to formula (I) as described herein for the treatment or prophylaxis of illnesses which are caused by disorders associated with the enzyme hormone-sensitive lipase.

The present invention relates to the use of a compound according to formula (I) as described above for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis The present invention particularly relates to the use of a compound according to formula (I) as described above for the treatment or prophylaxis of diabetes, metabolic syndrome, dyslipidemia, atherosclerosis or obesity.

A particular embodiment of the present invention is the use of a compound according to formula (I) as described above for the treatment or prophylaxis of diabetes.

A further particular embodiment of the present invention is the use of a compound according to formula (I) as described above for the treatment or prophylaxis of diabetes Type II.

Also an embodiment of the present invention is the use of a compound according to formula (I) as described above for the treatment or prophylaxis of cardiovascular diseases, myocardial dysfunction, inflammation, non-alcoholic fatty liver disease or non-alcoholic steatohepatitis.

A particular embodiment of the present invention is the use of a compound according to formula (I) as described above for the treatment or prophylaxis of non-alcoholic fatty liver disease or non-alcoholic steatohepatitis.

The present invention also relates to the use of a compound according to formula (I) as described above for the preparation of a medicament for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

The present invention particularly relates to the use of a compound according to formula (I) as described above for the preparation of a medicament for the treatment or prophylaxis of diabetes, metabolic syndrome, dyslipidemia, atherosclerosis or obesity.

A particular embodiment of the present invention is the use of a compound according to formula (I) as described above for the preparation of medicaments for the treatment or prophylaxis of diabetes.

A further particular embodiment of the present invention is the use of a compound according to formula (I) as described above for the preparation of medicaments for the treatment or prophylaxis of diabetes Type II.

Also an embodiment of the present invention is the use of a compound according to formula (I) as described above for the preparation of a medicament for the treatment or prophylaxis of cardiovascular diseases, myocardial dysfunction, inflammation, non-alcoholic fatty liver disease or non-alcoholic steatohepatitis.

A particular embodiment of the present invention is the use of a compound according to formula (I) as described above for the preparation of a medicament for the treatment or prophylaxis of non-alcoholic fatty liver disease or non-alcoholic steatohepatitis.

The present invention particularly relates to a compound according to formula (I) as described above for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis.

A particular embodiment of the present invention is a compound according to formula (I) as described above for the treatment or prophylaxis of diabetes, metabolic syndrome, dyslipidemia, atherosclerosis or obesity.

A further particular embodiment of the present invention is a compound according to formula (I) as described above for the treatment or prophylaxis of diabetes.

Also a further particular embodiment of the present invention is a compound according to formula (I) as described above for the treatment or prophylaxis of diabetes Type II.

Also a particular embodiment of the present invention is a compound according to formula (I) as described above for the treatment or prophylaxis of cardiovascular diseases, myocardial dysfunction, inflammation, non-alcoholic fatty liver disease or non-alcoholic steatohepatitis.

A further particular embodiment of the present invention is a compound according to formula (I) as described above for the treatment or prophylaxis of non-alcoholic fatty liver disease or non-alcoholic steatohepatitis.

Also an object of the invention is a method for the treatment or prophylaxis of diabetes, metabolic syndrome, dyslipidemia, atherosclerosis, obesity, cardiovascular diseases, myocardial dysfunction, inflammation, non-alcoholic fatty liver disease or non-alcoholic steatohepatitis, which method comprises administering an effective amount of a compound according to formula (I) as described above.

Also a particular object of the invention is a method for the treatment or prophylaxis of diabetes, metabolic syndrome, dyslipidemia, atherosclerosis or obesity, which method comprises administering an effective amount of a compound according to formula (I) as described above.

A particular embodiment of the present invention is a method for the treatment or prophylaxis of diabetes, which method comprises administering an effective amount of a compound according to formula (I) as described above.

A further particular embodiment of the present invention is a method for the treatment or prophylaxis of diabetes Type II, which method comprises administering an effective amount of a compound according to formula (I) as described above.

Also an embodiment of the present invention is a method for the treatment or prophylaxis of cardiovascular diseases, myocardial dysfunction, inflammation, non-alcoholic fatty liver disease or non-alcoholic steatohepatitis, which method comprises administering an effective amount of a compound according to formula (I) as described above.

Also a further embodiment of the present invention is a method for the treatment or prophylaxis of non-alcoholic fatty liver disease or non-alcoholic steatohepatitis, which method comprises administering an effective amount of a compound according to formula (I) as described above.

A further object of the present invention comprises a compound according to formula (I) as described herein, when manufactured according to any one of the described processes.

Assay Procedures

Production of Human Full Length Hormone Sensitive Lipase-His[6]:
1) Cloning: cDNA was prepared from commercial human brain polyA+RNA and used as a template in overlapping PCR to generate a full length human HSL ORF with a 3'-His6 tag.

This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His$^6$, 48 hr., containing 25 µM E-64. Cell count: $1.78 \times 10^{10}$ cells/ml, 90% viable.

Cells were thawed. On ice, cells were suspended in Base Buffer containing 10% glycerol, 25 mM Tris-Cl, 300 mM NaCl, 10 mM imidazole, 10 mM 2-mercaptoethanol, 2 µg pepstatin/ml, 2 µg leupeptin/ml, 2 µg antipain/ml, pH 8.0 at 4° C. in a final volume of 475 ml with $3.75 \times 10^7$ cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 µm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 µm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 µm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes).

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Example | HSL hum IC50 (uM) |
|---|---|
| 1 | 0.615 |
| 2 | 0.132 |
| 3 | 0.843 |
| 4 | 0.842 |
| 5 | 0.879 |
| 6 | 0.608 |
| 7 | 0.883 |
| 8 | 0.481 |
| 9 | 0.454 |
| 10 | 0.29 |
| 11 | 0.459 |
| 12 | 0.511 |
| 13 | 0.362 |
| 14 | 0.135 |
| 15 | 0.212 |
| 16 | 0.594 |
| 17 | 0.828 |
| 18 | 0.203 |
| 19 | 0.548 |
| 20 | 0.233 |
| 21 | 0.169 |
| 22 | 0.489 |
| 23 | 0.436 |
| 24 | 0.441 |
| 25 | 0.865 |
| 26 | 0.288 |
| 27 | 0.591 |
| 28 | 0.514 |
| 29 | 0.222 |
| 30 | 0.887 |
| 31 | 0.622 |
| 32 | 0.635 |
| 33 | 0.543 |
| 34 | 0.829 |

| Example | HSL hum IC50 (uM) |
|---------|-------------------|
| 35 | 0.305 |
| 36 | 0.367 |
| 37 | 0.877 |
| 38 | 0.834 |
| 39 | 0.298 |
| 40 | 0.0432 |

Compounds of formula (I) and their pharmaceutically acceptable salts or esters thereof as described above have $IC_{50}$ values between 0.0001 uM and 1000 uM, particular compounds have $IC_{50}$ values between 0.001 uM and 500 uM, further particular compounds have $IC_{50}$ values between 0.001 uM and 5 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

2-Chloro-N-[(6R,7aS)-3-oxo-2-(4-trifluoromethoxy-phenyl)-hexahydro-pyrrolo[1,2-c]imidazol-6-yl]-benzamide

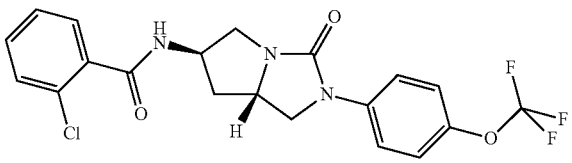 [SMILES: O=C(N[C@@H]1C[C@H]2CN(c3ccc(OC(F)(F)F)cc3)C(=O)N2C1)c1ccccc1Cl]

a) (2S,4R)-4-Hydroxy-1-(4-trifluoromethoxy-phenylcarbamoyl)-pyrrolidine-2-carboxylic acid methyl ester

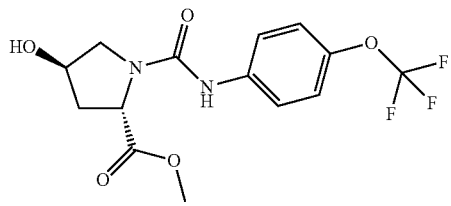 [SMILES: COC(=O)[C@@H]1C[C@@H](O)CN1C(=O)Nc1ccc(OC(F)(F)F)cc1]

Diisopropylethylamine (0.782 g, 5.5 mmol) was dropped into a suspension of compound (2S,4R)-4-Hydroxy-pyrrolidine-2-carboxylic acid methyl ester (1.0 g, 5.5 mmol) in anhydrous dichloromethane (50 mL), the mixture was stirred at room temperature for 10 minutes. 1-isocyanato-4-(trifluoromethoxy)benzene (1.116 g, 5.5 mmol) was added to the suspension and the mixture was continued to be stirred for 2 hours at room temperature. The mixture was poured into water (50 mL), the resulting mixture was filtrated. The liquid was extracted with dichloromethane (3×50 mL). The organic layers was combined, washed with brine (50 mL), dried over anhydrous sodium sulphate, filtered and concentrated. The residue combined with the filter cake yielded 1.86 g (97%) of the target compound. $^{1}$H NMR (300 MHz, CDCl$_{3}$): δ 7.41 (d, 2H, J=9.0 Hz), 7.14 (d, 2H, J=8.7 Hz), 6.59 (s, 1H), 4.64 (t, 2H, J=7.5 Hz), 3.78-3.73, (m, 4H), 3.59 (d, 1H, J=9.9 Hz), 2.36-2.21 (m, 2H); LC-MS: 349.1 [M+1]$^{+}$.

b) (2S,4R)-4-(tert-Butyl-diphenyl-silanyloxy)-1-(4-trifluoromethoxy-phenylcarbamoyl)-pyrrolidine-2-carboxylic acid methyl ester

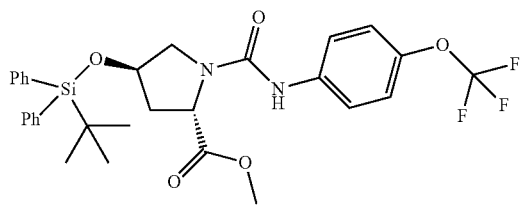 [SMILES: COC(=O)[C@@H]1C[C@@H](O[Si](c2ccccc2)(c2ccccc2)C(C)(C)C)CN1C(=O)Nc1ccc(OC(F)(F)F)cc1]

TBDPSCl (1.73 g, 6.3 mmol) was dropped into a solution of (2S,4R)-4-Hydroxy-1-(4-trifluoromethoxy-phenylcarbamoyl)-pyrrolidine-2-carboxylic acid methyl ester (1.0 g, 2.9 mmol) and imidazole (0.98 g, 14.4 mmol) in DMF (20 mL), the mixture was stirred at room temperature for 4 hours. Then the mixture was poured into water (50 mL), extracted with ethyl acetate (3×30 mL). The organic layers was combined, washed with water (2×30 mL), brine (30 mL), then dried over anhydrous sodium sulfate, filtered and concentrated. The residue was purified by silica gel column chromatography (ethyl acetate/petroleum ether=1:5) to give compound 1.48 g (88%) of the title compound. 1H NMR (300 MHz, CDCl3): δ 7.67-7.62 (m, 4H), 7.47-7.37 (m, 8H), 7.13 (d, 2H, J=8.7 Hz), 6.37 (s, 1H), 4.68-4.55 (m, 2H), 3.71 (s, 3H), 3.54-3.42 (m, 2H), 2.33-2.25 (m, 1H), 2.05-1.97 (m, 1H), 1.06 (s, 9H); LC-MS: 587.2 [M+1]$^+$.

c) (2S,4R)-4-(tert-Butyl-diphenyl-silanyloxy)-2-hydroxymethyl-pyrrolidine-1-carboxylic acid (4-trifluoromethoxy-phenyl)-amide

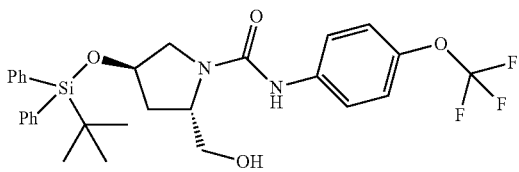 [SMILES: CC(C)(C)[Si](O[C@@H]1C[C@@H](CO)N(C(=O)Nc2ccc(OC(F)(F)F)cc2)C1)(c1ccccc1)c1ccccc1]

NaBH$_4$ (200 mg, 5.3 mmol) was added to a solution of (2S,4R)-4-(tert-Butyl-diphenyl-silanyloxy)-1-(4-trifluoromethoxy-phenylcarbamoyl)-pyrrolidine-2-carboxylic acid methyl ester (2.8 g, 4.8 mmol) in methanol (50 mL) portionwise. The mixture was stirred at room temperature for 4 hours. Then the mixture was poured into water (50 mL), extracted with ethyl acetate (3×50 mL). The organic layers was combined, washed with brine (50 mL), dried over anhydrous sodium sulphate, filtered and concentrated. The residue was purified by silica gel column chromatography (petroleum ether/ethyl acetate=5:1) to give 2.35 g (88%) of the title compound.

$^1$H NMR (300 MHz, CDCl$_3$): δ 7.66-7.62 (m, 4H), 7.46-7.28 (m, 8H), 7.08 (d, 2H, J=8.4 Hz), 4.35-4.23 (m, 2H), 3.65 (dd, 2H, J$_1$=11.1 Hz, J$_2$=2.1 Hz), 3.45 (t, 1H, J=9.3 Hz), 3.18-3.15 (m, 1H), 2.13-2.05 (m, 1H), 1.55-1.45 (m, 1H), 1.04 (s, 9H).

d) (6R,7aS)-6-(tert-Butyl-diphenyl-silanyloxy)-2-(4-trifluoromethoxy-phenyl)-hexahydro-pyrrolo[1,2-c]imidazol-3-one

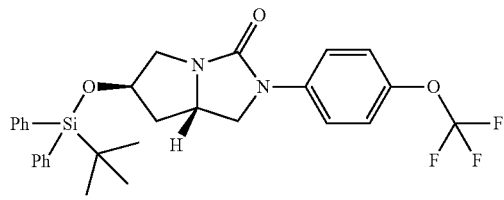 [SMILES: CC(C)(C)[Si](O[C@@H]1C[C@H]2CN(c3ccc(OC(F)(F)F)cc3)C(=O)N2C1)(c1ccccc1)c1ccccc1]

t-BuOK (1.0 g, 8.9 mmol) was added to a solution of (2S,4R)-4-(tert-Butyl-diphenyl-silanyloxy)-2-hydroxymethyl-pyrrolidine-1-carboxylic acid (4-trifluoromethoxy-phenyl)-amide (2.0 g, 3.6 mmol) in anhydrous THF (50 mL) at 0° C. The mixture was stirred for 15 minutes at 0° C. Then tosyl-chloride (0.88 g, 4.6 mmol) was added to the mixture, and the mixture was stirred for 30 minutes at 0° C. The mixture was poured into water (50 mL), extracted with ethyl acetate (3×50 mL). The organic layers was combined, washed with brine (50 mL), dried over anhydrous sodium sulphate, filtered and concentrated. The residue was purified by silicagel column chromatography (petroleum ether/ethyl acetate=10:1) to give 1.6 g (83%) of the title compound. $^1$H NMR (300 MHz, CDCl$_3$): δ 7.68-7.63 (m, 4H), 7.58 (d, 2H, J=9.3 Hz), 7.50-7.39 (m, 6H), 7.19 (d, 2H, J=9.0 Hz), 4.56 (t, 1H, J=5.1 Hz), 4.30-4.22 (m, 1H), 4.04 (t, 1H, J=8.4 Hz), 3.86 (dd, 1H, J$_1$=12.6 Hz, J$_2$=5.7), 3.67 (dd, 1H, J$_1$=9.3 Hz, J$_2$=2.4 Hz), 3.18 (d, 1H, J=12.6 Hz), 2.07 (dd, 1H, J$_1$=12.6, J$_2$=5.4), 1.46-1.37 (m, 1H), 1.11 (s, 9H).

e) (6R,7aS)-6-Hydroxy-2-(4-trifluoromethoxy-phenyl)-hexahydro-pyrrolo[1,2-c]imidazol-3-one

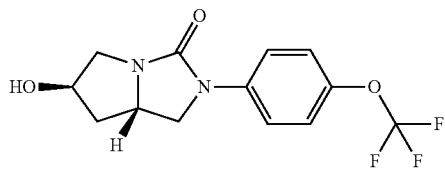 [SMILES: O=C1N(c2ccc(OC(F)(F)F)cc2)C[C@@H]2C[C@@H](O)CN12]

Tetrabutyl ammonium fluoride (1.0 g, 3.8 mmol) was added to a solution of (6R,7aS)-6-(tert-Butyl-diphenyl-silanyloxy)-2-(4-trifluoromethoxy-phenyl)-hexahydro-pyrrolo[1,2-c]imidazol-3-one (1.8 g, 3.3 mmol) in anhydrous THF (20 mL). The mixture was stirred for 2 hours at room temperature. The mixture was poured into water (50 mL), extracted with ethyl acetate (3×50 mL). The organic layers was combined, washed with brine (50 mL), dried over anhydrous sodium sulphate, filtered and concentrated. The residue was purified by silica gel column chromatography (MeOH/CH$_2$Cl$_2$=1:20) to give 0.95 g (94%) of the title compound.

$^1$H NMR (300 MHz, CDCl$_3$): δ 7.60 (d, 2H, J=9.3 Hz), 7.19 (d, 2H, J=9.0 Hz), 4.65-4.61 (m, 1H), 4.22-4.13 (m, 1H), 4.10-4.02 (m, 2H), 3.73 (dd, 1H, J$_1$=9.3 Hz, J$_2$=2.4 Hz), 3.15-3.10 (m, 1H), 2.11 (dd, 1H, J$_1$=12.6 Hz, J$_2$=5.1 Hz), 1.64-1.54 (m, 1H); LC-MS: 303.0 [M+1]$^+$.

f) (6S,7aS)-6-Bromo-2-(4-trifluoromethoxy-phenyl)-hexahydro-pyrrolo[1,2-c]imidazol-3-one

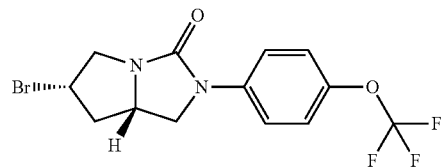 [SMILES: O=C1N(c2ccc(OC(F)(F)F)cc2)C[C@@H]2C[C@H](Br)CN12]

Triphenylphosphine (1.7 g, 6.5 mmol) was added to a solution of (6R,7aS)-6-Hydroxy-2-(4-trifluoromethoxy-phenyl)-hexahydro-pyrrolo[1,2-c]imidazol-3-one (1.0 g, 3.3 mmol) and CBr$_4$ (2.2 g, 6.6 mmol) in anhydrous THF (50 mL), the mixture was stirred at room temperature for 30 minutes under N$_2$ protection. Then the mixture was filtered and concentrated. The residue was purified by silica column chromatography (petroleum ether/ethyl acetate=3:1) to give 1.15 g (95%) of the title compound. ¹H NMR (300 MHz, CDCl₃): δ 7.61 (d, 2H, J=9.3 Hz), 7.21 (d, 2H, J=8.4 Hz), 4.48-4.42 (m, 1H), 4.19 (dd, 1H, $J_1$=13.2 Hz, $J_2$=2.7 Hz), 4.11-4.02 (m, 2H), 3.92-3.88 (m, 1H), 3.53 (dd, 1H, $J_1$=13.5 Hz, $J_2$=5.4 Hz), 2.81-2.71 (m, 1H), 2.26-2.18 (m, 1H). LC-MS: 365.0 [M+1]⁺.

g) (6R,7aS)-6-Azido-2-(4-trifluoromethoxy-phenyl)-hexahydro-pyrrolo[1,2-c]imidazol-3-one

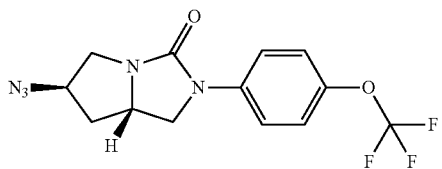 [SMILES: [N-]=[N+]=N[C@@H]1C[C@H]2CN(c3ccc(OC(F)(F)F)cc3)C(=O)N2C1]

Sodium azide (80 mg, 1.2 mmol) was added to a solution of (6S,7aS)-6-Bromo-2-(4-trifluoromethoxy-phenyl)-hexahydro-pyrrolo[1,2-c]imidazol-3-one (350 mg, 1.0 mmol) in anhydrous DMF (10 mL), the mixture was heated to 70° C. and stirred for 2 hours. The mixture was cooled and poured into water (30 mL), extracted with ethyl acetate (3×20 mL), the organic layers was combined and washed with water (2×20 mL), brine (20 mL), dried over anhydrous sodium sulphate, filtered and concentrated. The residue was purified by silica gel column chromatography (eluting with petroleum ether/ethyl acetate=10:1) to give 260 mg (83%) of the title compound. ¹H NMR (300 MHz, CDCl₃): δ 7.59 (d, 2H, J=9.3 Hz), 7.19 (d, 2H, J=8.4 Hz), 4.33 (t, 1H, J=6.3 Hz), 4.13-3.98 (m, 3H), 3.75-3.72 (m, 1H), 3.15 (dd, 1H, $J_1$=12.6 Hz, $J_2$=2.1 Hz), 2.19 (dd, 1H, $J_1$=13.2 Hz, $J_2$=3.9 Hz), 1.73-1.63 (m, 1H).

h) (6R,7aS)-6-Amino-2-(4-trifluoromethoxy-phenyl)-hexahydro-pyrrolo[1,2-c]imidazol-3-one

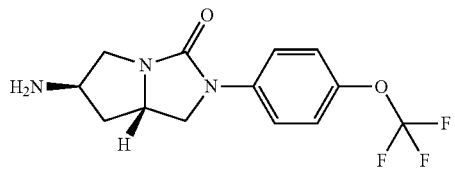 [SMILES: N[C@@H]1C[C@H]2CN(c3ccc(OC(F)(F)F)cc3)C(=O)N2C1]

10% Pd/C (20 mg, 20%) was added to a solution of (6R,7aS)-6-Azido-2-(4-trifluoromethoxy-phenyl)-hexahydro-pyrrolo[1,2-c]imidazol-3-one (100 mg, 0.3 mmol) in THF (10 mL), the mixture stirred for 30 minutes under H₂. The mixture was filtered and concentrated. The residue was purified by silica gel column chromatography (dichloromethane/methnol=20:1) to give 80 mg (87%) of the title compound. LC-MS: 302.1 [M+1]⁺.

i) 2-Chloro-N-[(6R,7aS)-3-oxo-2-(4-trifluoromethoxy-phenyl)-hexahydro-pyrrolo[1,2-c]imidazol-6-yl]-benzamide 2-Chloro-benzoyl chloride (40.5 mg, 0.23 mmol) was dropped into a solution of (6R,7aS)-6-Amino-2-(4-trifluoromethoxy-phenyl)-hexahydro-pyrrolo[1,2-c]imidazol-3-one (70 mg, 0.23 mmol) and DIPEA (23 mg, 0.23 mmol) in anhydrous dichloromethane (3 mL), the mixture was stirred at room temperature for 4 hours. Then the mixture was poured into water (10 mL) extracted with ethyl acetate (3×10 mL), the organic layers was combined, washed with brine (20 mL), dried over anhydrous sodium sulfate, filtered and concentrated. The residue was purified by silica gel column chromatography (petroleum ether/ethyl acetate=5:1) to give 85 mg (83%) of the title compound. ¹H NMR (300 MHz, CDCl₃): δ 7.70-7.67 (m, 1H), 7.60 (d, 2H, J=9.3 Hz), 7.43-7.32 (m, 3H), 7.20 (d, 2H, J=9.0 Hz), 6.49 (d, 1H, J=6.6 Hz), 4.76-4.68 (m, 1H), 4.26 (dd, 1H, $J_1$=12.6 Hz, $J_2$=7.2 Hz), 4.18-4.02 (m, 2H), 3.76 (dd, 1H, $J_1$=9 Hz, $J_2$=2.1 Hz), 3.13 (dd, 1H, $J_1$=12.9 Hz, $J_2$=3.3 Hz), 2.35-2.28 (m, 1H), 1.93-1.83 (m, 1H); LC-MS: 440.1 [M+1]⁺.

Example 2

2-Chloro-N-[(6R,7aS)-3-oxo-2-(4-trifluoromethoxy-phenyl)-hexahydro-pyrrolo[1,2-c]imidazol-6-yl]-benzenesulfonamide

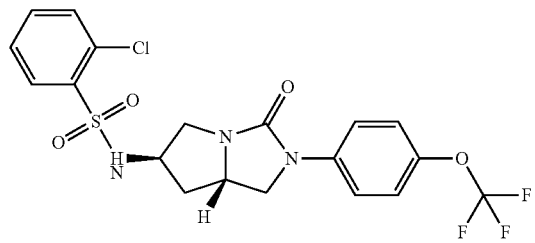 [SMILES: O=C1N(c2ccc(OC(F)(F)F)cc2)C[C@@H]2C[C@@H](NS(=O)(=O)c3ccccc3Cl)CN12]

In analogy to the procedure described for the synthesis of 2-Chloro-N-[(6R,7aS)-3-oxo-2-(4-trifluoromethoxy-phenyl)-hexahydro-pyrrolo[1,2-c]imidazol-6-yl]-benzamide (example 1, step i) the title compound was prepared from (6R,7aS)-6-Amino-2-(4-trifluoromethoxy-phenyl)-hexahydro-pyrrolo[1,2-c]imidazol-3-one (example 1, step h) and 2-chlorobenzene-1-sulfonyl chloride to yield 27% the title compound. ¹H NMR (300 MHz, CDCl₃): δ 8.13 (d, 1H, J=7.2 Hz), 7.58-7.45 (m, 6H), 7.19 (d, 2H, J=9.0 Hz), 5.33 (d, 1H, J=6.3 Hz), 4.06-3.98 (m, 3H), 3.94-3.85 (m, 1H), 3.66 (d, 1H, J=6.9 Hz), 2.94 (dd, 1H, $J_1$=12.9 Hz, $J_2$=3.6 Hz), 2.19-2.12 (m, 1H), 1.74-1.64 (m, 1H); LC-MS: 476.0 [M+1]⁺.

Example 3

(6R,7aS)-6-(Toluene-4-sulfonyl)-2-(4-trifluoromethoxy-phenyl)-hexahydro-pyrrolo[1,2-c]imidazol-3-one

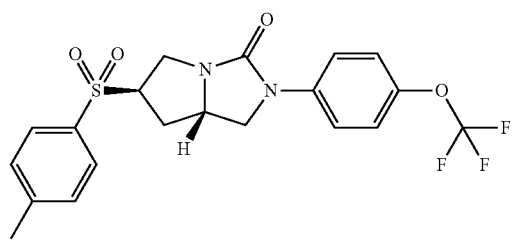 [SMILES: Cc1ccc(S(=O)(=O)[C@@H]2C[C@H]3CN(c4ccc(OC(F)(F)F)cc4)C(=O)N3C2)cc1]

a) (6R,7aS)-6-p-Tolylsulfanyl-2-(4-trifluoromethoxy-phenyl)-hexahydro-pyrrolo[1,2-c]imidazol-3-one

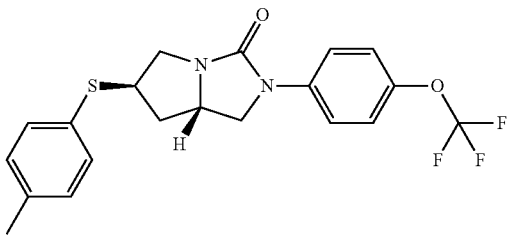 [SMILES: Cc1ccc(S[C@@H]2C[C@H]3CN(c4ccc(OC(F)(F)F)cc4)C(=O)N3C2)cc1]

Na (112 mg, 0.548 mmol) was added to anhydrous ethanol (10 ml). Until the sodium was dissolved. 4-methylbenzenethiol (34 mg, 0.0274 mmol) was added in the ice-bath. Subsequently (6S,7aS)-6-Bromo-2-(4-trifluoromethoxy-phenyl)-hexahydro-pyrrolo[1,2-c]imidazol-3-one (100 mg, 0.274 mmol) was added. After the addition, the ice bath was removed and the reaction was stirred for overnight at the room temperature. The reaction mixture was concentrated under reduced pressure. The residue was purified by silica gel column chromatography to yield 100 mg (85%) of the title compounds as white solid. $^1$H NMR (300 MHz, CDCl$_3$): δ 7.61-7.56 (m, 2H), 7.33-7.29 (m, 2H), 7.20-7.12 (m, 4H), 4.28-4.00 (m, 3H), 3.85-3.83 (m, 1H), 3.69 (dd, 1H, $J_1$=2.7 Hz, $J_2$=9.6 Hz), 3.11 (dd, 1H, $J_1$=4.2 Hz, $J_2$=12.9 Hz), 2.32 (s, 3H), 2.19-2.12 (m, 1H), 1.93-1.83 (m, 1H); LC-MS: 409 [M+1]$^+$.

b) (6R,7aS)-6-(Toluene-4-sulfonyl)-2-(4-trifluoromethoxy-phenyl)-hexahydro-pyrrolo[1,2-c]imidazol-3-one (6R,7aS)-6-p-Tolylsulfanyl-2-(4-trifluoromethoxy-phenyl)-hexahydro-pyrrolo[1,2-c]imidazol-3-one (100 mg, 0.245 mmol) in DCM (5 mL) was added dropwise to a solution of m-CPBA (169.6 mg, 0.980 mmol) in DCM (15 mL) at 0° C. The reaction mixture was stirred for 2 hours at the room temperature. The reaction mixture was quenched with aq. Na$_2$SO$_3$ (20 mL), the organic layer was washed with sat. NaCl (50 mL), dried over anhydrous Na$_2$SO$_4$ and evaporated to dryness. The residue was purified by silica gel column chromatography to give 25 mg (23%) of the title compound as white solid. $^1$H NMR (300 MHz, CDCl$_3$): δ 7.78 (d, 2H, J=7.8 Hz), 7.56 (d, 2H, J=8.7 Hz), 7.39 (d, 2H, J=7.8 Hz), 7.17 (d, 2H, J=8.7 Hz), 4.12-3.98 (m, 3H), 3.76 (s, 1H), 3.68 (d, 1H, J=9.3 Hz), 3.49 (dd, 1H, $J_1$=5.4 Hz, $J_2$=13.2 Hz), 2.68 (d, 1H, J=3.3 Hz), 2.48 (s, 1H), 1.83 (d, 1H, J=13.5 Hz); LC-MS: 441 [M+1]$^+$.

Example 4

(6R,7aS)-6-(3-Methyl-butane-1-sulfonyl)-2-(4-trifluoromethoxy-phenyl)-hexahydro-pyrrolo[1,2-c]imidazol-3-one

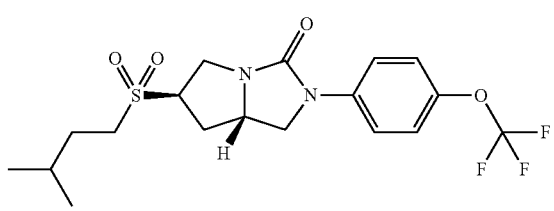 [SMILES: CC(C)CCS(=O)(=O)[C@@H]1C[C@H]2CN(c3ccc(OC(F)(F)F)cc3)C(=O)N2C1]

In analogy to the procedure described for the synthesis of (6R,7aS)-6-(Toluene-4-sulfonyl)-2-(4-trifluoromethoxy-phenyl)-hexahydro-pyrrolo[1,2-c]imidazol-3-one (example 3) the title compound was prepared from (6S,7aS)-6-Bromo-2-(4-trifluoromethoxy-phenyl)-hexahydro-pyrrolo[1,2-c]imidazol-3-one, 3-Methyl-butane-1-thiol and subsequent oxidation of the intermediate with m-CPBA to yield the title compound. $^1$H NMR (300 MHz, CDCl$_3$): δ 7.62-7.58 (m, 2H), 7.21 (d, 2H, J=9 Hz), 4.32 (dd, 1H, $J_1$=8.7 Hz, $J_2$=12.9 Hz), 4.13-4.02 (m, 2H), 3.75-3.66 (m, 2H), 3.54 (dd, 1H, $J_1$=5.7 Hz, $J_2$=12.9 Hz), 2.98 (t, 2H, J=8.1 Hz), 2.76-2.69 (m, 1H), 1.95-1.84 (m, 2H), 1.75 (t, 2H, J=6 Hz), 0.98 (s, 1H); LC-MS: 421 [M+1]$^+$.

Example 5

(6R,7aS)-6-(4-Fluoro-benzenesulfonyl)-2-(4-trifluoromethoxy-phenyl)-hexahydro-pyrrolo[1,2-c]imidazol-3-one

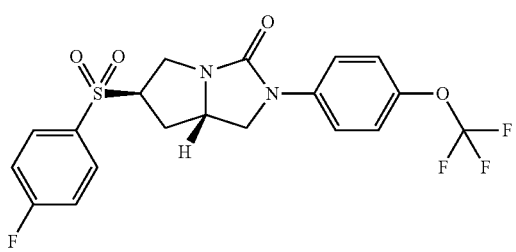 [SMILES: O=C1N(c2ccc(OC(F)(F)F)cc2)C[C@@H]2C[C@@H](S(=O)(=O)c3ccc(F)cc3)CN12]

In analogy to the procedure described for the synthesis of (6R,7aS)-6-(Toluene-4-sulfonyl)-2-(4-trifluoromethoxy-phenyl)-hexahydro-pyrrolo[1,2-c]imidazol-3-one (example 3) the title compound was prepared from (6S,7aS)-6-Bromo-2-(4-trifluoromethoxy-phenyl)-hexahydro-pyrrolo[1,2-c]imidazol-3-one, 4-Fluoro-benzenethiol and subsequent oxidation of the intermediate with m-CPBA to yield the title compound. $^1$H NMR (300 MHz, CDCl$_3$): δ 7.96-7.92 (m, 2H), 7.59-7.54 (m, 2H), 7.32-7.26 (m, 2H), 7.18 (d, 2H, J=8.4 Hz), 4.16-4.00 (m, 3H), 3.49 (dd, 2H, $J_1$=5.7 Hz, $J_2$=13.2 Hz), 2.75-2.67 (m, 1H), 1.91-1.80 (m, 1H). LC-MS: 445 [M+1]$^+$.

Example 6

(6R,7aS)-6-(1-Phenyl-ethoxy)-2-(4-trifluoromethoxy-phenyl)-hexahydro-pyrrolo[1,2-c]imidazol-3-one

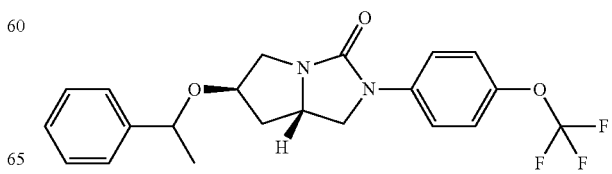

NaH (70% in oil, 7 mg, 0.2 mmol) was added to a solution of (6R,7aS)-6-Hydroxy-2-(4-trifluoromethoxy-phenyl)-hexahydro-pyrrolo[1,2-c]imidazol-3-one (example 1, step e) (50 mg, 0.165 mmol) and (1-Bromo-ethyl)-benzene (40 mg, 0.21 mmol) in anhydrous THF (10 mL), the mixture was refluxed overnight. The mixture was cooled and poured into water (20 mL), extracted with ethyl acetate (3×20 mL), the organic layers was combined, washed with brine, dried over anhydrous sodium sulfate, filtered and concentrated. The residue was purified by silica gel column chromatography (petroleum ether/ethyl acetate=7:1) to give 20 mg (30%) of the title compound. $^1$H NMR (300 MHz, CDCl$_3$): δ 7.57 (dd, 2H, J$_1$=9.0 Hz, J$_2$=1.8 Hz), 7.38-7.26 (m, 5H), 7.17 (d, 2H, J=9.0 Hz), 4.52-4.42 (m, 1H), 4.12-3.84 (m, 4H), 3.71-3.61 (m, 1H), 3.27-3.06 (m, 1H), 2.28-2.02 (m, 1H), 1.49-1.37 (m, 4H); LC-MS: 407.0 [M+1]$^+$.

Example 7

Propyl-carbamic acid (6R,7aS)-3-oxo-2-(4-trifluoromethoxy-phenyl)-hexahydro-pyrrolo[1,2-c]imidazol-6-yl ester

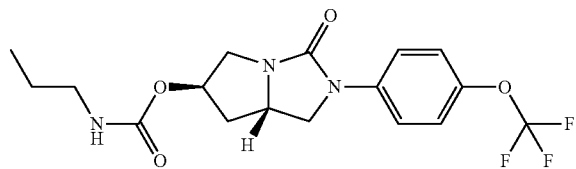 [SMILES: CCCNC(=O)O[C@@H]1C[C@H]2CN(c3ccc(OC(F)(F)F)cc3)C(=O)N2C1]

1-Isocyanatopropane (30 mg, 0.4 mmol) was added to a solution of (6R,7aS)-6-Hydroxy-2-(4-trifluoromethoxy-phenyl)-hexahydro-pyrrolo[1,2-c]imidazol-3-one (example 1, step e) (60 mg, 0.2 mmol) in anhydrous THF (10 mL) and pyridine (2 mL). The mixture was refluxed overnight. The mixture was cooled and poured into water (20 mL), extracted with ethyl acetate (3×20 mL). The organic layers was combined, washed with brine (20 mL), dried over anhydrous sodium sulfate, filtered and concentrated. The residue was purified by silica gel column chromatography (petroleum ether/ethyl acetate=4:1) to give final compound 20 mg (26%) of the title compound. $^1$H NMR (300 MHz, CDCl$_3$): δ 7.60 (d, 2H, J=9.0 Hz), 7.19 (d, 2H, J=8.7 Hz), 5.35 (t, 1H, J=5.7), 4.71 (s, 1H), 4.17-4.00 (m, 3H), 3.74 (d, 1H, J=7.2 Hz), 3.22-3.12 (m, 3H), 2.23 (dd, 1H, J$_1$=12.9 Hz, J$_2$=3.3 Hz), 1.71-1.48 (m, 3H), 0.94 (t, 3H, J=7.2 Hz); LC-MS: 388.1 [M+1]$^+$.

Example 8

(4-Fluoro-benzyl)-carbamic acid (6R,7aS)-3-oxo-2-(4-trifluoromethoxy-phenyl)-hexahydro-pyrrolo[1,2-c]imidazol-6-yl ester

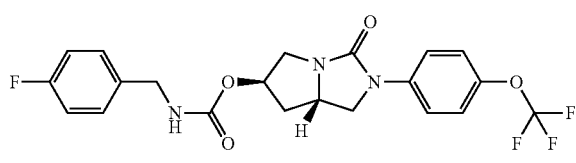 [SMILES: O=C(NCc1ccc(F)cc1)O[C@@H]1C[C@H]2CN(c3ccc(OC(F)(F)F)cc3)C(=O)N2C1]

Diisopropylethylamine (800 mg, 6.2 mmol) and (4-fluorophenyl)methanamine (400 mg, 3.2 mmol) was dropped into a solution of bis(trichloromethyl) carbonate (300 mg, 1 mmol) in anhydrous dichloromethane (30 mL) at −78° C., the mixture was stirred for 2 hours at room temperature. Then (6R,7aS)-6-Hydroxy-2-(4-trifluoromethoxy-phenyl)-hexahydro-pyrrolo[1,2-c]imidazol-3-one (example 1, step e) (50 mg, 0.165 mmol) was added into the mixture, the mixture was refluxed for 2 days. The mixture was cooled and poured into water (50 mL), extracted with ethyl acetate (3×30 mL), the organic layers was combined washed with brine (30 mL), dried over anhydrous sodium sulfate, filtered and concentrated. The residue was purified by silica gel column chromatography (petroleum ether/ethyl acetate=5:1) to yield 25 mg (33%) of the title compound. $^1$H NMR (300 MHz, CDCl$_3$): δ 7.60 (d, 2H, J=9.3 Hz), 7.29-7.24 (m, 2H), 7.19 (d, 2H, J=8.4 Hz), 7.03 (t, 2H, J=8.7 Hz), 5.38 (t, 1H, J=5.7 Hz), 5.04 (s, 1H), 4.34 (d, 2H, J=5.7 Hz), 4.15 (dd, 1H, J$_1$=13.5 Hz, J$_2$=6.0 Hz), 4.05-4.00 (m, 1H), 3.74 (d, 1H, J=6.9 Hz), 3.2 (d, 1H, J=13.5 Hz), 2.27-2.21 (m, 1H), 1.78-1.63 (m, 1H); LC-MS: 454.1 [M+1]$^+$.

Example 9

N-[(6R,7aS)-3-Oxo-2-(4-trifluoromethoxy-phenyl)-hexahydro-pyrrolo[1,2-c]imidazol-6-yl]-C-phenyl-methanesulfonamide

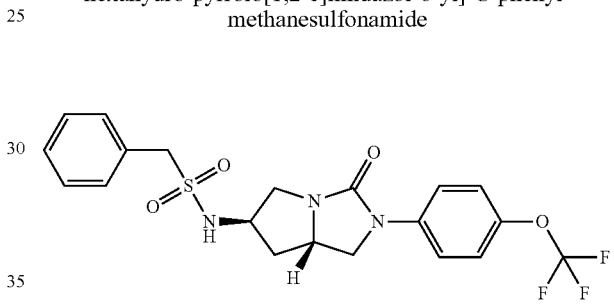

(6R,7aS)-6-Amino-2-(4-trifluoromethoxy-phenyl)-hexahydro-pyrrolo[1,2-c]imidazol-3-one (example 1, step h) (100 mg, 0.33 mmol), phenylmethanesulfonyl chloride (125 mg, 0.66 mmol) and Et$_3$N (0.1 g, 0.99 mmol) were added to dichloromethane (3 mL), and the mixture was stirred for 12 hours. The mixture was directly purified by prep-TLC (DCM/MeOH=30:1) to yield 100 mg (67%) of the title compound. $^1$H NMR (300 MHz, CDCl$_3$): δ 7.58-7.55 (m, 2H), 7.43-7.40 (m, 5H), 7.20-7.17 (m, 2H), 4.40-4.37 (m, 1H), 4.29 (s, 2H), 4.05-3.97 (m, 4H), 3.68-3.62 (m, 1H), 2.85-2.81 (m, 1H), 2.11-2.07 (m, 1H), 1.78-1.72 (m, 1H); LC-MS: 456.1 [M+1]$^+$.

Example 10

4-Methyl-N-[(6R,7aS)-3-oxo-2-(4-trifluoromethoxy-phenyl)-hexahydro-pyrrolo[1,2-c]imidazol-6-yl]-benzenesulfonamide

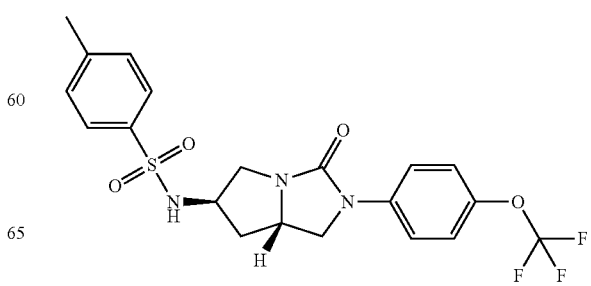

In analogy to the procedure described for the synthesis of N-[(6R,7aS)-3-Oxo-2-(4-trifluoromethoxy-phenyl)-hexahydro-pyrrolo[1,2-c]imidazol-6-yl]-C-phenyl-methane-sulfonamide (example 9) the title compound was prepared from (6R,7aS)-6-Amino-2-(4-trifluoromethoxy-phenyl)-hexahydro-pyrrolo[1,2-c]imidazol-3-one (example 1, step h) and 4-Methyl-benzenesulfonyl chloride. $^1$H NMR (300 MHz, CDCl$_3$): δ 7.75 (d, 2H, J=8.1 Hz), 7.55 (d, 2H, J=7.2 Hz), 7.33 (d, 2H, J=8.4 Hz), 7.17 (d, 2H, J=8.7 Hz), 4.93-4.91 (m, 1H), 4.01-3.97 (m, 4H), 3.67-3.62 (m, 1H), 2.84-2.81 (m, 1H), 2.45 (s, 3H), 2.18-2.16 (m, 1H), 1.79-1.72 (m, 1H); LC-MS: 456.1 [M+1]$^+$.

Example 11

2-Methyl-propane-1-sulfonic acid [(6R,7aS)-3-oxo-2-(4-trifluoromethoxy-phenyl)-hexahydro-pyrrolo[1,2-c]imidazol-6-yl]-amide

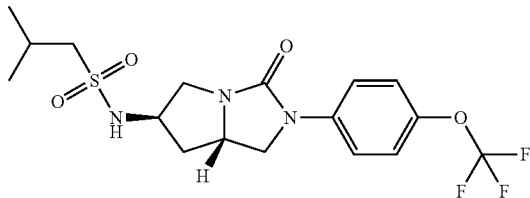 [SMILES: CC(C)CS(=O)(=O)N[C@@H]1C[C@H]2CN(c3ccc(OC(F)(F)F)cc3)C(=O)N2C1]

In analogy to the procedure described for the synthesis of N-[(6R,7aS)-3-Oxo-2-(4-trifluoromethoxy-phenyl)-hexahydro-pyrrolo[1,2-c]imidazol-6-yl]-C-phenyl-methane-sulfonamide (example 9) the title compound was prepared from (6R,7aS)-6-Amino-2-(4-trifluoromethoxy-phenyl)-hexahydro-pyrrolo[1,2-c]imidazol-3-one (example 1, step h) and 2-Methyl-propane-1-sulfonyl chloride. $^1$H NMR (300 MHz, CDCl$_3$): δ 7.58-7.52 (m 2H), 7.19 (d, 2H, J=8.4 Hz), 4.48-4.44 (m, 1H), 4.25-4.04 (m, 4H), 4.20-4.18 (m, 1H), 3.74-3.71 (m, 1H), 3.02-2.94 (m, 3H), 2.30-2.21 (m, 2H), 1.90-1.87 (m, 1H), 1.13 (d, 6H, J=6.9 Hz); LC-MS: 422.1 [M+1]$^+$.

Example 12

3-Chloro-N-[(6R,7aS)-3-oxo-2-(4-trifluoromethoxy-phenyl)-hexahydro-pyrrolo[1,2-c]imidazol-6-yl]-benzenesulfonamide

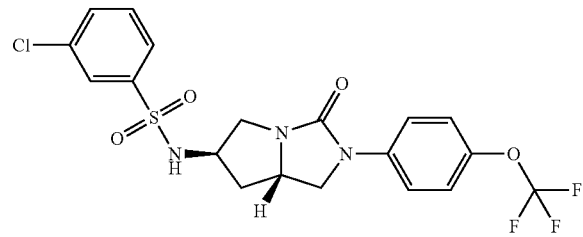 [SMILES: O=C1N(c2ccc(OC(F)(F)F)cc2)C[C@@H]2C[C@@H](NS(=O)(=O)c3cccc(Cl)c3)CN12]

In analogy to the procedure described for the synthesis of N-[(6R,7aS)-3-Oxo-2-(4-trifluoromethoxy-phenyl)-hexahydro-pyrrolo[1,2-c]imidazol-6-yl]-C-phenyl-methane-sulfonamide (example 9) the title compound was prepared from (6R,7aS)-6-Amino-2-(4-trifluoromethoxy-phenyl)-hexahydro-pyrrolo[1,2-c]imidazol-3-one (example 1, step h) and 3-Chloro-benzenesulfonyl chloride. $^1$H NMR (300 MHz, CDCl$_3$): δ 7.83-7.72 (m, 2H), 7.58-7.43 (m, 4H), 7.16-7.14 (d, 2H, J=9.3 Hz), 5.19-5.17 (m, 1H), 4.07-3.92 (m, 4H), 3.66-3.64 (m, 1H), 2.86-2.84 (m, 1H), 2.15-2.13 (m, 1H), 1.70-1.67 (m, 1H); LC-MS: 476.1 [M+1]$^+$.

Example 13

4-Chloro-N-[(6R,7aS)-3-oxo-2-(4-trifluoromethoxy-phenyl)-hexahydro-pyrrolo[1,2-c]imidazol-6-yl]-benzenesulfonamide

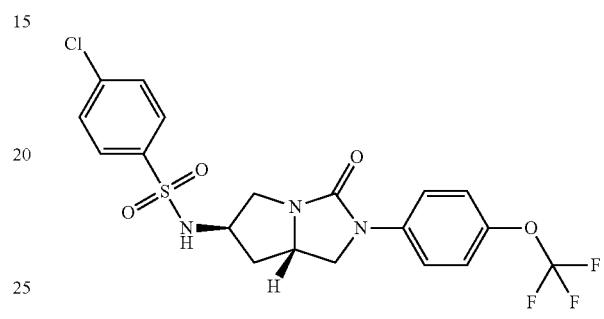

In analogy to the procedure described for the synthesis of N-[(6R,7aS)-3-Oxo-2-(4-trifluoromethoxy-phenyl)-hexahydro-pyrrolo[1,2-c]imidazol-6-yl]-C-phenyl-methane-sulfonamide (example 9) the title compound was prepared from (6R,7aS)-6-Amino-2-(4-trifluoromethoxy-phenyl)-hexahydro-pyrrolo[1,2-c]imidazol-3-one (example 1, step h) and 4-Chloro-benzenesulfonyl chloride. $^1$H NMR (300 MHz, CDCl$_3$): δ 7.79 (d, 2H, J=8.4 Hz), 7.53-7.48 (m, 4H), 7.15 (d, 2H, J=9.0 Hz), 4.85 (s, 1H), 4.05-3.97 (m, 4H), 3.64-3.62 (m, 1H), 2.88-2.85 (m, 1H), 2.18-2.16 (m, 1H) 1.58-1.54 (m, 1H); LC-MS: 476.1 [M+1]$^+$.

Example 14

2-Fluoro-N-[(6R,7aS)-3-oxo-2-(4-trifluoromethoxy-phenyl)-hexahydro-pyrrolo[1,2-c]imidazol-6-yl]-benzenesulfonamide

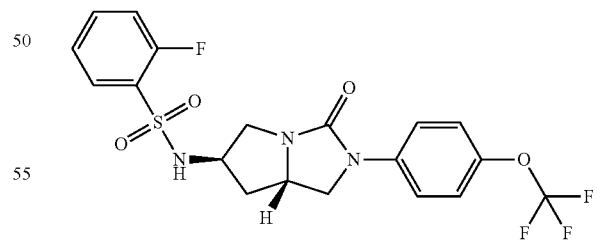

In analogy to the procedure described for the synthesis of N-[(6R,7aS)-3-Oxo-2-(4-trifluoromethoxy-phenyl)-hexahydro-pyrrolo[1,2-c]imidazol-6-yl]-C-phenyl-methane-sulfonamide (example 9) the title compound was prepared from (6R,7aS)-6-Amino-2-(4-trifluoromethoxy-phenyl)-hexahydro-pyrrolo[1,2-c]imidazol-3-one (example 1, step h) and 2-Fluoro-benzenesulfonyl chloride. $^1$H NMR (300 MHz, CDCl$_3$): δ 7.93-7.90 (m, 1 Hz), 7.63-7.52 (m, 3H), 7.32-7.14

(m, 4H), 5.07-5.05 (m, 1H), 4.05-3.97 (m, 4H), 3.63-3.61 (m, 1H), 2.95-2.92 (m, 1H), 2.15-2.13 (m, 1H), 1.71-1.68 (m, 1H); LC-MS: 460.1 [M+1]$^+$.

Example 15

2-Chloro-pyridine-3-sulfonic acid [(6R,7aS)-3-oxo-2-(4-trifluoromethoxy-phenyl)-hexahydro-pyrrolo[1,2-c]imidazol-6-yl]-amide

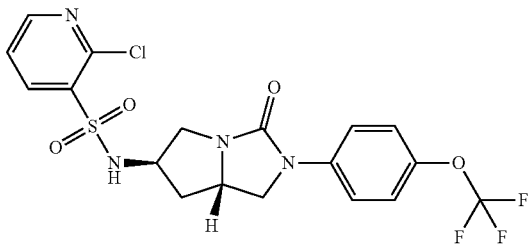 [SMILES: O=C1N(c2ccc(OC(F)(F)F)cc2)C[C@@H]2C[C@@H](NS(=O)(=O)c3cccnc3Cl)CN12]

In analogy to the procedure described for the synthesis of N-[(6R,7aS)-3-Oxo-2-(4-trifluoromethoxy-phenyl)-hexahydro-pyrrolo[1,2-c]imidazol-6-yl]-C-phenyl-methane-sulfonamide (example 9) the title compound was prepared from (6R,7aS)-6-Amino-2-(4-trifluoromethoxy-phenyl)-hexahydro-pyrrolo[1,2-c]imidazol-3-one (example 1, step h) and 2-Chloro-pyridine-3-sulfonyl chloride. $^1$H NMR (300 MHz, CDCl$_3$): δ 8.60-8.58 (m, 1H), 8.41-8.38 (m, 1H), 7.52-7.43 (m, 3H), 7.14-7.10 (m, 2H), 5.45-5.43 (m, 1H), 4.06-3.87 (m, 4H), 3.65-3.62 (m, 1H), 2.95-2.93 (m, 1H), 2.05-2.01 (m, 1H), 1.58-1.54 (m, 1H); LC-MS: 477.0 [M+1]$^+$.

Example 16

2-Hydroxy-pyridine-3-sulfonic acid [(6R,7aS)-3-oxo-2-(4-trifluoromethoxy-phenyl)-hexahydro-pyrrolo[1,2-c]imidazol-6-yl]-amide

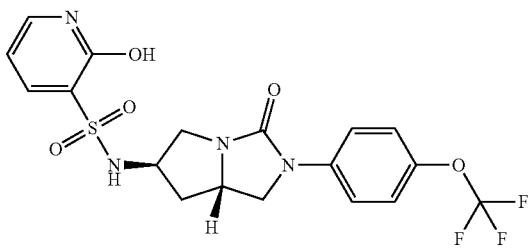 [SMILES: O=C1N(c2ccc(OC(F)(F)F)cc2)C[C@@H]2C[C@@H](NS(=O)(=O)c3cccnc3O)CN12]

2-Chloro-pyridine-3-sulfonic acid [(6R,7aS)-3-oxo-2-(4-trifluoromethoxy-phenyl)-hexahydro-pyrrolo[1,2-c]imidazol-6-yl]-amide (example 15) (100 mg, 0.21 mmol) was added to concentrated hydrochloric acid (10 mL, 12 M), the mixture was stirred for 24 h at 100° C. To the mixture was added sat. NaHCO$_3$ to adjust to pH=8. Then extracted with ethyl acetate (15 mL×2), dried over anhydrous sodium sulfate and concentrated. The residue was directly purified by pre-TLC (dichloromethane:MeOH=100:1) to yield 20 mg (21%) of the title compound. $^1$H NMR (300 MHz, CDCl$_3$): δ 12.0 (bs, 1H) 8.22-8.19 (m, 1 Hz), 7.85-7.80 (m, 1H), 7.46-7.41 (m, 2H), 7.11-7.08 (m, 2 Hz), 6.49-6.41 (m, 2H), 4.09-3.91 (m, 4H), 3.63-3.61 (m, 1H), 3.04-3.01 (m, 1H), 2.22-2.20 (m, 1H), 1.64-1.62 (m, 1H); LC-MS: 459.0 [M+1]$^+$.

Example 17

1-Methyl-3-[(6R,7aS)-3-oxo-2-(4-trifluoromethoxy-phenyl)-hexahydro-pyrrolo[1,2-c]imidazol-6-yl]-1-propyl-urea

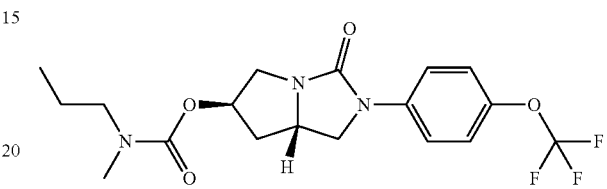

Triphosgene (29 mg, 0.3 mmol) was added to a solution of (6R,7aS)-6-Hydroxy-2-(4-trifluoromethoxy-phenyl)-hexahydro-pyrrolo[1,2-c]imidazol-3-one (example 1, step e) (100 mg, 0.33 mmol) in dichloromethane (10 mL) at −30° C., the mixture was stirred for 0.5 h at the same temperature, and continued to stir for another 0.5 h at 20° C., then N-methyl-propan-1-amine (24 mg, 0.3 mmol) was added. The mixture was stirred overnight at room temperature. The mixture was concentrated and directly to purified by prep-TLC (dichloromethane/MeOH=50:1) to yield 70 mg (53%) of the title compound. $^1$H NMR (300 MHz, CDCl$_3$): δ 7.56 (d, 2H, J=9.3 Hz), 7.15 (d, 2H, J=9.0 Hz), 4.59-4.56 (m, 1H), 4.39 (s, 1H), 4.17-3.98 (m, 3H), 3.69-3.65 (m, 1H), 3.19-3.16 (m, 2H), 3.01-2.98 (m, 1H), 2.86 (s, 3H), 2.14-2.13 (m, 1H), 1.79-1.75 (m, 1H), 1.56 (q, 2H, J=7.5 Hz), 0.89 (t, 3H, J=7.5 Hz); LC-MS: 401.1 [M+1]$^+$.

Example 18

1-(3-Fluoro-phenyl)-1-methyl-3-[(6R,7aS)-3-oxo-2-(4-trifluoromethoxy-phenyl)-hexahydro-pyrrolo[1,2-c]imidazol-6-yl]-urea

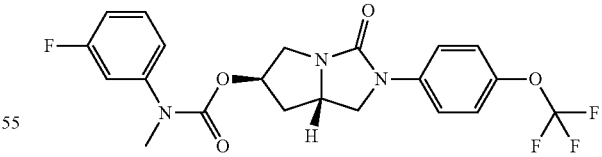

In analogy to the procedure described for the synthesis of 1-Methyl-3-[(6R,7aS)-3-oxo-2-(4-trifluoromethoxy-phenyl)-hexahydro-pyrrolo[1,2-c]imidazol-6-yl]-1-propyl-urea (example 17) the title compound was prepared from (6R,7aS)-6-Hydroxy-2-(4-trifluoromethoxy-phenyl)-hexahydro-pyrrolo[1,2-c]imidazol-3-one (example 1, step e) and (3-Fluoro-phenyl)-methyl-amine. $^1$H NMR (300 MHz, CDCl$_3$): δ 7.56-7.52 (m, 2H), 7.42-7.40 (m, 1H), 7.16-6.93 (m, 5H), 4.47-4.36 (m, 2H), 4.13-3.90 (m, 2H), 3.66-3.62 (m, 1H), 4.04-4.01 (m, 1H), 3.24 (s, 3H), 2.83-2.80 (m, 1H), 2.09-2.04 (m, 1H), 1.75-1.70 (m, 1H); LC-MS: 453.1 [M+1]$^+$.

Example 19

3-Chloro-N-[(6R,7aS)-3-oxo-2-(4-trifluoromethoxy-phenyl)-hexahydro-pyrrolo[1,2-c]imidazol-6-yl]-benzamide

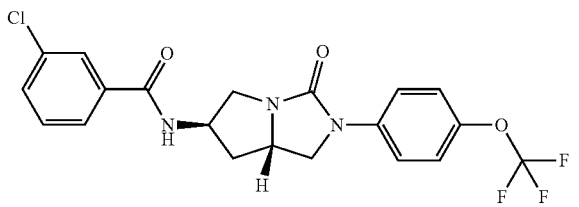 [SMILES: O=C(N[C@@H]1C[C@H]2CN(c3ccc(OC(F)(F)F)cc3)C(=O)N2C1)c1cccc(Cl)c1]

In analogy to the procedure described for the synthesis of 2-Chloro-N-[(6R,7aS)-3-oxo-2-(4-trifluoromethoxy-phenyl)-hexahydro-pyrrolo[1,2-c]imidazol-6-yl]-benzamide (example 1, step i) the title compound was prepared from (6R,7aS)-6-Amino-2-(4-trifluoromethoxy-phenyl)-hexahydro-pyrrolo[1,2-c]imidazol-3-one (example 1, step h) and 3-Chloro-benzoyl chloride. $^1$H NMR (300 MHz, CDCl$_3$): δ 7.73-7.34 (m, 6H), 7.16-7.13 (m, 2H), 6.32 (s, 1H), 4.86 (s, 1H), 4.25-4.01 (m, 3H), 3.73-3.72 (m, 1H), 3.13-3.11 (m, 1H), 2.24-2.22 (m, 1H), 1.91-1.90 (m, 1H); LC-MS: 441.1 [M+1]$^+$.

Example 20

4-Methyl-N-[(6S,7aS)-3-oxo-2-(4-trifluoromethoxy-phenyl)-hexahydro-pyrrolo[1,2-c]imidazol-6-yl]-benzenesulfonamide

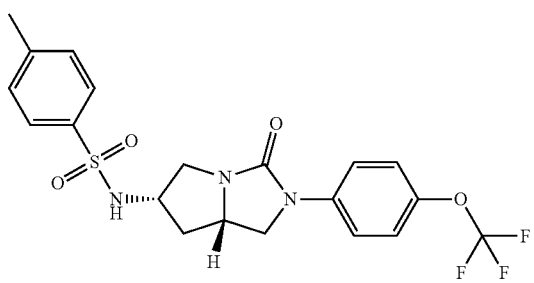 [SMILES: Cc1ccc(S(=O)(=O)N[C@H]2C[C@H]3CN(c4ccc(OC(F)(F)F)cc4)C(=O)N3C2)cc1]

a) (6S,7aS)-6-Hydroxy-2-(4-trifluoromethoxy-phenyl)-hexahydro-pyrrolo[1,2-c]imidazol-3-one

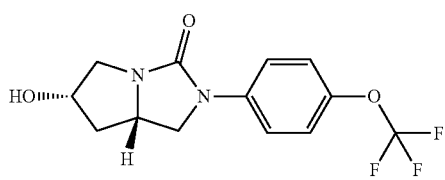 [SMILES: O=C1N(c2ccc(OC(F)(F)F)cc2)C[C@@H]2C[C@H](O)CN12]

In analogy to the procedure described for the synthesis of (6R,7aS)-6-Hydroxy-2-(4-trifluoromethoxy-phenyl)-hexahydro-pyrrolo[1,2-c]imidazol-3-one (example 1, step e) the title compound was prepared starting from (2S,4S)-4-Hydroxy-1-methylcarbamoyl-pyrrolidine-2-carboxylic acid methyl ester. $^1$H NMR (300 MHz, CDCl$_3$): δ 7.50 (d, 2H, J=9.3 Hz), 7.14 (d, 2H, J=9.0 Hz), 4.47 (brs, 1H), 4.00-3.71 (m, 4H), 3.08 (dd, 1H, J$_1$=12.9 Hz, J$_2$=3.9 Hz), 2.61 (s, 1H), 2.35-2.26 (m, 1H), 1.77-1.70 (m, 1H); LC-MS: 303.0 [M+1]$^+$.

b) (6R,7aS)-6-Bromo-2-(4-trifluoromethoxy-phenyl)-hexahydro-pyrrolo[1,2-c]imidazol-3-one

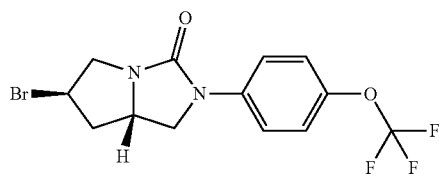 [SMILES: O=C1N(c2ccc(OC(F)(F)F)cc2)C[C@@H]2C[C@@H](Br)CN12]

To the solution of (6S,7aS)-6-Hydroxy-2-(4-trifluoromethoxy-phenyl)-hexahydro-pyrrolo[1,2-c]imidazol-3-one (example 20, step a) (1.47 g, 4.36 mmol) and CBr$_4$ (3.3 g, 8.72 mmol) in anhydrous THF (30 mL) was added PPh$_3$ (2.3 g, 8.72 mmol) in THF (10 mL). Then the mixture was filtered and concentrated. The residue was purified by silica gel column chromatography (eluting with petroleum ether/ethyl acetate=10:1) to yield 1.50 g (84%) of the title compound as white solid. $^1$H NMR (300 MHz, CDCl$_3$): δ 7.58 (d, 2H, J=9 Hz), 7.17 (d, 2H, J=9 Hz), 4.59-4.55 (m, 1H), 4.43-4.37 (m, 1H), 4.25-4.22 (m, 1H), 4.07 (t, 1H, J=9 Hz), 3.76 (dd, 1H, J$_1$=3 Hz, J$_2$=9 Hz), 3.62-3.56 (d, 1H, J=18 Hz), 2.43 (dd, 1H, J$_1$=6 Hz J$_2$=12 Hz), 1.99-1.92 (m, 1H). LC-MS: 365 [M+1]$^+$.

c) (6S,7aS)-6-Azido-2-(4-trifluoromethoxy-phenyl)-hexahydro-pyrrolo[1,2-c]imidazol-3-one

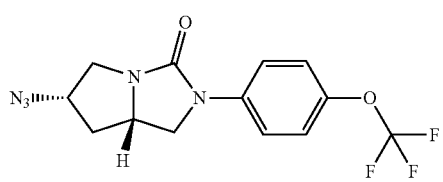 [SMILES: [N-]=[N+]=N[C@H]1C[C@H]2CN(c3ccc(OC(F)(F)F)cc3)C(=O)N2C1]

The mixture of (6R,7aS)-6-Bromo-2-(4-trifluoromethoxy-phenyl)-hexahydro-pyrrolo[1,2-c]imidazol-3-one (example 20, step b) (1.45 g, 4 mmol) and NaN$_3$ (0.34 g, 5.2 mmol) in DMF (50 mL) was heated to 70° C. for 1.5 h. Then to the mixture was added water (100 mL) and extracted with EtOAc (100 mL×2), the organic layer was washed water (100 mL) and brine (100 mL). The combined organic layer was evaporated to dryness and the crude product (1.0 g, 77%) was used without further purification in the next step.

d) (6S,7aS)-6-Amino-2-(4-trifluoromethoxy-phenyl)-hexahydro-pyrrolo[1,2-c]imidazol-3-one

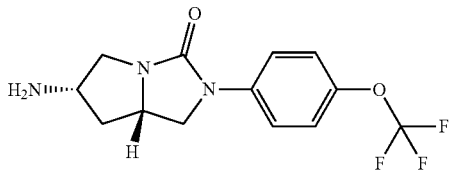 [SMILES: N[C@H]1C[C@H]2CN(c3ccc(OC(F)(F)F)cc3)C(=O)N2C1]

A mixture of crude (6S,7aS)-6-Azido-2-(4-trifluoromethoxy-phenyl)-hexahydro-pyrrolo[1,2-c]imidazol-3-one (example 20, step c) (0.90 g) and 10% Pd/C (0.18 g) was stirred in anhydrous THF (20 mL) at the $H_2$ atmosphere for 1 h at 15° C. The mixture was filtered, concentrated and purified by silica gel column chromatography (eluting with DCM/MeOH=50:1~10:1) to yield 0.70 g of the title compound as a grey solid. $^1$H NMR (300 MHz, $d_6$-DMSO): δ 7.67 (d, 2H, J=3 Hz), 7.31 (d, 2H, J=9 Hz), 3.96 (d, 1H, J=12 Hz), 3.86 (d, 1H, J=12 Hz), 3.77-3.73 (m, 1H), 3.54-3.52 (m, 1H), 3.18-3.17 (m, 1H), 3.10-3.06 (m, 1H), 2.15-2.11 (m, 1H), 1.69 (s, 2H), 1.35-1.31 (m, 1H); LC-MS: 302.1 [M+1]$^+$.

e) 4-Methyl-N-[(6S,7aS)-3-oxo-2-(4-trifluoromethoxy-phenyl)-hexahydro-pyrrolo[1,2-c]imidazol-6-yl]-benzenesulfonamide A mixture of (6S,7aS)-6-Amino-2-(4-trifluoromethoxy-phenyl)-hexahydro-pyrrolo[1,2-c]imidazol-3-one (example 20, step d) (80 mg, 0.266 mmol), 4-Methyl-benzenesulfonyl chloride (101 mg, 0.53 mmol) and NEt$_3$ (100 mg, 0.99 mmol) in DCM (10 mL) was stirred at 10° C. overnight. The mixture was washed with water (5 mL×3), dried with anhydrous sodium sulfate and then purified with silica gel column chromatography (eluting with DCM/MeOH=150:1) to 58 mg (46%) of the title compound as a white solid. $^1$H NMR (300 MHz, CDCl$_3$): δ 7.72 (d, 2H, J=9 Hz), 7.31 (d, 2H, J=9 Hz), 7.24 (d, 2H, J=6 Hz), 7.04 (d, 2H, J=9 Hz), 6.00 (d, 1H, J=9 Hz), 4.07-4.00 (m, 1H) 3.76-3.74 (m, 2H), 3.49-3.36 (m, 2H), 3.22-3.19 (m, 1H), 2.47 (s, 3H), 2.23-2.15 (m, 1H), 1.55-1.44 (m, 1H); LC-MS: 456.1 [M+1]$^+$.

Example 21

4-Chloro-N-[(6R,7aS)-3-oxo-2-(4-trifluoromethoxy-phenyl)-hexahydro-pyrrolo[1,2-c]imidazol-6-yl]-benzamide

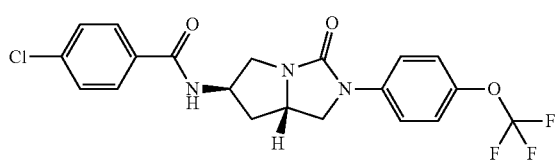 [SMILES: O=C(N[C@@H]1C[C@H]2CN(c3ccc(OC(F)(F)F)cc3)C(=O)N2C1)c1ccc(Cl)cc1]

In analogy to the procedure described for the synthesis of 2-Chloro-N-[(6R,7aS)-3-oxo-2-(4-trifluoromethoxy-phenyl)-hexahydro-pyrrolo[1,2-c]imidazol-6-yl]-benzamide (example 1, step i) the title compound was prepared from (6R,7aS)-6-Amino-2-(4-trifluoromethoxy-phenyl)-hexahydro-pyrrolo[1,2-c]imidazol-3-one (example 1, step h) and 4-Chloro-benzoyl chloride. $^1$H NMR (300 MHz, CDCl$_3$): δ 7.68 (d, 2H, J=8.4 Hz), 7.58 (d, 2H, J=9.0 Hz), 7.54 (d, 2H, J=8.7 Hz), 7.40 (d, 2H, J=8.4 Hz), 6.23 (s, 1H), 4.65 (s, 1H), 4.25-4.22 (m, 1H), 4.08-4.05 (m, 2H), 3.74-3.71 (m, 1H), 3.10-3.08 (m, 1H), 2.24-2.21 (m, 1H) 1.88-1.86 (m, 1H); LC-MS: 441.1 [M+1]$^+$.

Example 22

2-Fluoro-N-[(6R,7aS)-3-oxo-2-(4-trifluoromethoxy-phenyl)-hexahydro-pyrrolo[1,2-c]imidazol-6-yl]-benzamide

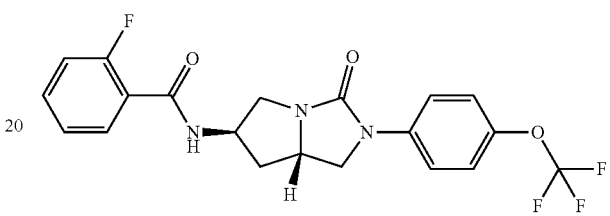

In analogy to the procedure described for the synthesis of 2-Chloro-N-[(6R,7aS)-3-oxo-2-(4-trifluoromethoxy-phenyl)-hexahydro-pyrrolo[1,2-c]imidazol-6-yl]-benzamide (example 1, step i) the title compound was prepared from (6R,7aS)-6-Amino-2-(4-trifluoromethoxy-phenyl)-hexahydro-pyrrolo[1,2-c]imidazol-3-one (example 1, step h) and 2-Fluoro-benzoyl chloride. $^1$H NMR (300 MHz, CDCl$_3$): δ 8.09-8.07 (m 1H), 7.61-7.46 (m, 3H), 7.28-7.08 (m, 4H), 6.88-6.85 (m, 1H), 4.71 (s, 1H), 4.28-4.25 (m, 1H), 4.10-4.07 (m, 2H), 3.75-3.72 (m, 1H), 3.12-3.10 (m, 1H), 2.27-2.24 (m, 1H) 1.86-1.83 (m, 1H); LC-MS: 424.1 [M+1]$^+$.

Example 23

4-Chloro-N-[(6S,7aS)-3-oxo-2-(4-trifluoromethoxy-phenyl)-hexahydro-pyrrolo[1,2-c]imidazol-6-yl]-benzenesulfonamide

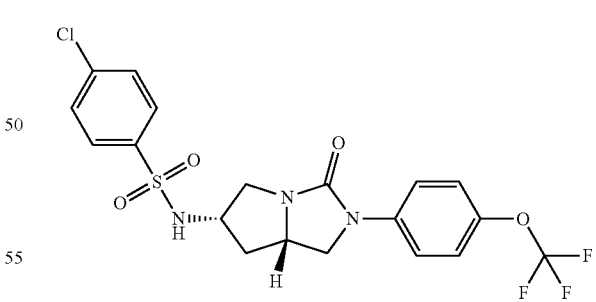

In analogy to the procedure described for the synthesis of 4-Methyl-N-[(6S,7aS)-3-oxo-2-(4-trifluoromethoxy-phenyl)-hexahydro-pyrrolo[1,2-c]imidazol-6-yl]-benzenesulfonamide (example 20) the title compound was prepared from (6S,7aS)-6-Amino-2-(4-trifluoromethoxy-phenyl)-hexahydro-pyrrolo[1,2-c]imidazol-3-one (example 20, step d) and 4-Chloro-benzenesulfonyl chloride. $^1$H NMR (300 MHz, CDCl$_3$): δ 7.80 (d, 2H, J=9 Hz), 7.44 (d, 2H, J=9 Hz), 7.35 (d, 2H, J=9 Hz), 7.08 (d, 2H, J=9 Hz), 6.24 (d, 1H, J=6

Hz), 4.08-4.02 (m, 1H), 3.85-3.77 (m, 2H), 3.56-3.46 (m, 2H), 3.29-3.22 (m, 1H), 2.31-2.25 (m, 1H), 1.58-1.47 (m, 1H); LC-MS: 476.0 [M+1]⁺.

Example 24

3,3-Dimethyl-N-[(6R,7aS)-3-oxo-2-(4-trifluoromethoxy-phenyl)-hexahydro-pyrrolo[1,2-c]imidazol-6-yl]-butyramide

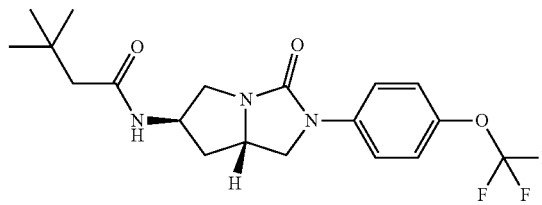

In analogy to the procedure described for the synthesis of 2-Chloro-N-[(6R,7aS)-3-oxo-2-(4-trifluoromethoxy-phenyl)-hexahydro-pyrrolo[1,2-c]imidazol-6-yl]-benzamide (example 1, step i) the title compound was prepared from (6R,7aS)-6-Amino-2-(4-trifluoromethoxy-phenyl)-hexahydro-pyrrolo[1,2-c]imidazol-3-one (example 1, step h) and 3,3-Dimethyl-butyryl chloride. ¹H NMR (300 MHz, CDCl₃): δ 7.60-7.54 (m, 2H), 7.19 (d, 2H, J=8.7 Hz), 5.53-5.50 (m, 1H), 4.50 (s, 1H), 4.20-4.18 (m, 1H), 4.07-4.03 (m, 2H), 3.72-3.70 (m, 1H), 2.98-2.96 (m, 1H), 2.17-2.05 (m, 3H), 1.82-1.79 (m, 1H), 1.05 (s, 9H); LC-MS: 400.1 [M+1]⁺.

Example 25

2-Chloro-pyridine-3-sulfonic acid [(6S,7aS)-3-oxo-2-(4-trifluoromethoxy-phenyl)-hexahydro-pyrrolo[1,2-c]imidazol-6-yl]-amide

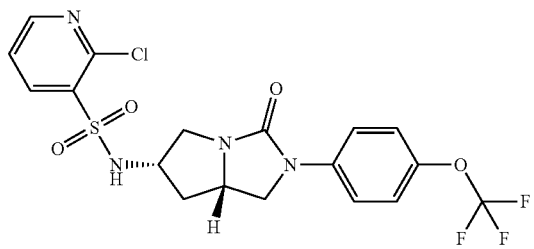 [SMILES: O=C1N(c2ccc(OC(F)(F)F)cc2)C[C@@H]2C[C@H](NS(=O)(=O)c3cccnc3Cl)CN12]

In analogy to the procedure described for the synthesis of 4-Methyl-N-[(6S,7aS)-3-oxo-2-(4-trifluoromethoxy-phenyl)-hexahydro-pyrrolo[1,2-c]imidazol-6-yl]-benzenesulfonamide (example 20) the title compound was prepared from (6S,7aS)-6-Amino-2-(4-trifluoromethoxy-phenyl)-hexahydro-pyrrolo[1,2-c]imidazol-3-one (example 20, step d) and 2-Chloro-pyridine-3-sulfonyl chloride. ¹H NMR (300 MHz, CDCl₃): δ 8.57 (d, 1H, J=3 Hz), 8.41 (d, 1H, J=12 Hz), 7.45-7.37 (m, 3H), 7.09, (d, 2H, J=6 Hz), 6.50 (d, 1H, J=9 Hz), 4.14-4.11 (m, 1H), 3.85-3.78 (m, 2H), 3.68-3.57 (m, 2H), 3.39-3.33 (m, 1H), 2.28-2.24 (m, 1H) 1.71-1.66 (m, 1H); LC-MS: 476.9 [M+1]⁺.

Example 26

N-[(6R,7aS)-3-Oxo-2-(4-trifluoromethoxy-phenyl)-hexahydro-pyrrolo[1,2-c]imidazol-6-yl]-2-phenoxy-acetamide

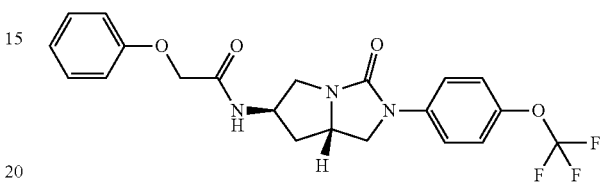

In analogy to the procedure described for the synthesis of 2-Chloro-N-[(6R,7aS)-3-oxo-2-(4-trifluoromethoxy-phenyl)-hexahydro-pyrrolo[1,2-c]imidazol-6-yl]-benzamide (example 1, step i) the title compound was prepared from (6R,7aS)-6-Amino-2-(4-trifluoromethoxy-phenyl)-hexahydro-pyrrolo[1,2-c]imidazol-3-one (example 1, step h) and Phenoxy-acetyl chloride. ¹H NMR (300 MHz, CDCl₃): δ 7.58-7.54 (m, 2H), 7.34-7.23 (m, 4H), 7.05-6.89 (m, 3H), 6.73-6.71 (m, 1H), 4.73-4.58 (m, 3H), 4.23-4.21 (m, 1H), 4.04-4.01 (m, 2H), 3.71-3.69 (m, 1H), 3.05-3.02 (m, 1H), 2.13-2.10 (m, 1H), 1.85-1.82 (m, 1H); LC-MS: 436.1 [M+1]⁺.

Example 27

2-tert-Butoxy-N-[(6R,7aS)-3-oxo-2-(4-trifluoromethoxy-phenyl)-hexahydro-pyrrolo[1,2-c]imidazol-6-yl]-acetamide

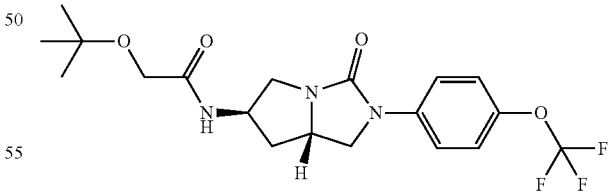

In analogy to the procedure described for the synthesis of 2-Chloro-N-[(6R,7aS)-3-oxo-2-(4-trifluoromethoxy-phenyl)-hexahydro-pyrrolo[1,2-c]imidazol-6-yl]-benzamide (example 1, step i) the title compound was prepared from (6R,7aS)-6-Amino-2-(4-trifluoromethoxy-phenyl)-hexahydro-pyrrolo[1,2-c]imidazol-3-one (example 1, step h) and tert-Butoxy-acetyl chloride. ¹H NMR (300 MHz, CDCl₃): δ 7.60-7.54 (m, 2H), 7.19 (d, 2H, J=8.7 Hz), 5.53-5.50 (m, 1H), 4.50 (s, 1H), 4.20-4.18 (m, 1H), 4.07-4.03 (m, 2H), 3.72-3.70

(m, 1H), 2.98-2.96 (m, 1H), 2.17-2.05 (m, 3H), 1.82-1.79 (m, 1H), 1.05 (s, 9H); LC-MS: 400.1 [M+1]+.

Example 28

3-Chloro-N-[(6S,7aS)-3-oxo-2-(4-trifluoromethoxy-phenyl)-hexahydro-pyrrolo[1,2-c]imidazol-6-yl]-benzenesulfonamide

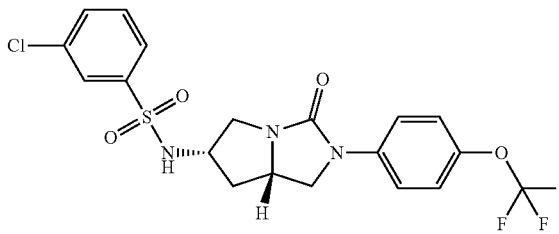

In analogy to the procedure described for the synthesis of 4-Methyl-N-[(6S,7aS)-3-oxo-2-(4-trifluoromethoxy-phenyl)-hexahydro-pyrrolo[1,2-c]imidazol-6-yl]-benzenesulfonamide (example 20) the title compound was prepared from (6S,7aS)-6-Amino-2-(4-trifluoromethoxy-phenyl)-hexahydro-pyrrolo[1,2-c]imidazol-3-one (example 20, step d) and 3-Chloro-benzenesulfonyl chloride. ¹H NMR (300 MHz, CDCl₃): δ 7.86 (d, 1H, J=3 Hz), 7.74 (t, 1H, J=3 Hz), 7.54 (d, 1H, J=9 Hz), 7.44-7.34 (m, 3H), 7.07 (d, 2H, J=9 Hz), 5.88 (d, 1H, J=9 Hz), 4.11-4.05 (m, 1H), 3.86-3.77 (m, 2H), 3.54 (d, 1H, J=9 Hz), 3.47-3.41 (m, 1H), 3.29-3.23 (m, 1H), 2.31-2.27 (m, 1H), 1.59-1.49 (m, 1H); LC-MS: 475.8 [M+1]+.

Example 29

2-Fluoro-N-[(6S,7aS)-3-oxo-2-(4-trifluoromethoxy-phenyl)-hexahydro-pyrrolo[1,2-c]imidazol-6-yl]-benzenesulfonamide

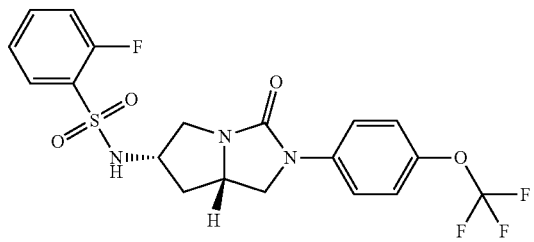 [SMILES: O=C1N(c2ccc(OC(F)(F)F)cc2)C[C@@H]2C[C@H](NS(=O)(=O)c3ccccc3F)CN12]

In analogy to the procedure described for the synthesis of 4-Methyl-N-[(6S,7aS)-3-oxo-2-(4-trifluoromethoxy-phenyl)-hexahydro-pyrrolo[1,2-c]imidazol-6-yl]-benzenesulfonamide (example 20) the title compound was prepared from (6S,7aS)-6-Amino-2-(4-trifluoromethoxy-phenyl)-hexahydro-pyrrolo[1,2-c]imidazol-3-one (example 20, step d) and 2-Fluoro-benzenesulfonyl chloride. ¹H NMR (300 MHz, CDCl₃): δ 7.88 (m, 1H), 7.58 (m, 1H), 7.37 (d, 2H, J=6 Hz), 7.29-7.15 (m, 3H), 7.07 (d, 1H, J=6 Hz), 5.87 (d, 1H, J=6 Hz), 4.20-4.14 (m, 1H), 3.84-3.75 (m, 2H), 3.54-3.47 (m, 2H), 3.32-3.25 (m, 1H), 2.30-2.22 (m, 1H), 1.63-1.53 (m, 1H); LC-MS: 459.9 [M+1]+.

Example 30

2-Methyl-propane-1-sulfonic acid [(6S,7aS)-3-oxo-2-(4-trifluoromethoxy-phenyl)-hexahydro-pyrrolo[1,2-c]imidazol-6-yl]-amide

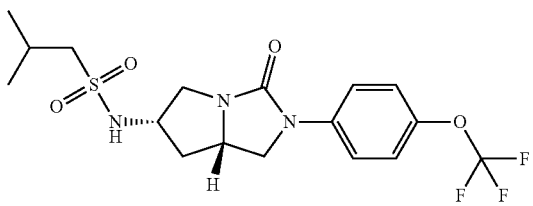 [SMILES: CC(C)CS(=O)(=O)N[C@H]1C[C@H]2CN(c3ccc(OC(F)(F)F)cc3)C(=O)N2C1]

In analogy to the procedure described for the synthesis of 4-Methyl-N-[(6S,7aS)-3-oxo-2-(4-trifluoromethoxy-phenyl)-hexahydro-pyrrolo[1,2-c]imidazol-6-yl]-benzenesulfonamide (example 20) the title compound was prepared from (6S,7aS)-6-Amino-2-(4-trifluoromethoxy-phenyl)-hexahydro-pyrrolo[1,2-c]imidazol-3-one (example 20, step d) and 2-Methyl-propane-1-sulfonyl chloride. ¹H NMR (300 MHz, CDCl₃): δ 7.53 (d, 2H, J=6 Hz), 7.17 (d, 2H, J=9 Hz), 4.80 (s, 1H), 4.25-4.18 (m, 1H), 3.97-3.72 (m, 2H), 3.64-3.62 (m, 2H), 3.51-3.47 (m, 1H), 2.93 (d, 2H, J=6 Hz), 2.55-2.53 (m, 1H), 2.26-2.24 (m, 1H), 1.57-1.55 (m, 1H), 1.09 (d, 6H, J=6 Hz); LC-MS: 422.1 [M+1]+.

Example 31

N-[(6S,7aS)-3-Oxo-2-(4-trifluoromethoxy-phenyl)-hexahydro-pyrrolo[1,2-c]imidazol-6-yl]-C-phenyl-methanesulfonamide

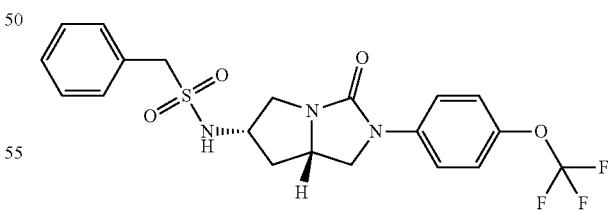

In analogy to the procedure described for the synthesis of 4-Methyl-N-[(6S,7aS)-3-oxo-2-(4-trifluoromethoxy-phenyl)-hexahydro-pyrrolo[1,2-c]imidazol-6-yl]-benzenesulfonamide (example 20) the title compound was prepared from (6S,7aS)-6-Amino-2-(4-trifluoromethoxy-phenyl)-hexahydro-pyrrolo[1,2-c]imidazol-3-one (example 20, step d) and Phenyl-methanesulfonyl chloride. ¹H NMR (300 MHz, CDCl₃): δ 7.44-7.34 (m, 7H), 7.12 (d, 2H, J=9 Hz), 5.39 (d, 1H, J=2.6), 4.26 (d, 2H, J=1.5 Hz), 3.83-3.42 (m, 5H), 3.21-3.18 (m, 1H), 2.24-2.32 (m, 1H), 1.28-1.67 (m, 1H); LC-MS: 456.0 [M+1]+.

Example 32

(6R,7aS)-6-(2-Hydroxy-pentyloxy)-2-(4-trifluoromethoxy-phenyl)-hexahydro-pyrrolo[1,2-c]imidazol-3-one

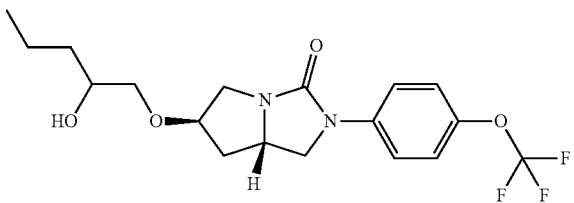 [SMILES: CCCC(O)CO[C@@H]1C[C@H]2CN(c3ccc(OC(F)(F)F)cc3)C(=O)N2C1]

NaH (25 mg, 70% in oil, 0.7 mmol) was added to a solution of (6R,7aS)-6-Hydroxy-2-(4-trifluoromethoxy-phenyl)-hexahydro-pyrrolo[1,2-c]imidazol-3-one (example 1, step e) (300 mg, 1 mmol) in anhydrous THF (10 mL), the mixture was stirred at room temperature for 0.5 hour, then 2-propyloxirane (300 mg, 3.5 mmol) was added to the solution, the mixture was stirred at 75° C. overnight in a sealed tube. The mixture was cooled and poured into water (50 mL), extracted with ethyl acetate (3×30 mL), the organic layers was combined and washed with brine, dried over anhydrous sodium sulphate, filtered and concentrated. The residue was purified by silica gel column chromatography (eluting with petroleum ether/ethyl acetate=4:1) to yield 100 mg (26%) of the title compound. $^1$H NMR (300 MHz, CDCl$_3$): δ 7.62 (d, 2H, J=8.7 Hz), 7.19 (d, 2H, J=8.7 Hz), 4.20 (t, 1H, J=5.7 Hz), 4.09-4.00 (m, 3H), 3.82-3.74 (m, 2H), 3.52-3.43 (m, 1H), 3.37-3.18 (m, 2H), 2.26-2.10 (m, 2H), 1.60-1.38 (m, 5H), 0.96 (t, 3H, J=6.9 Hz); LC-MS: 389.1 [M+1]+.

Example 33

(6S,7aR)-6-(3-Methyl-butoxy)-2-[4-(2,2,2-trifluoro-ethoxy)-phenyl]-hexahydro-pyrrolo[1,2-c]imidazol-3-one

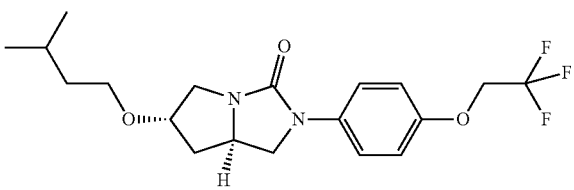 [SMILES: CC(C)CCO[C@H]1C[C@@H]2CN(c3ccc(OCC(F)(F)F)cc3)C(=O)N2C1]

a) 1-Isocyanato-4-(2,2,2-trifluoro-ethoxy)-benzene

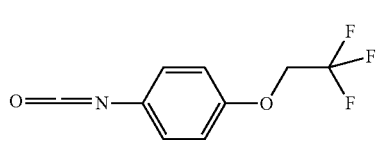

To a mixture of NaH (60% dispersion, 3.12 g, 78.01 mmol) in DMF (60 mL) at 0° C. was added 2,2,2-Trifluoro-ethanol (7.09 g, 70.09 mmol) and stirred for 30 min. A solution of 1-Fluoro-4-nitro-benzene (10 g, 70.09 mmol) in DMF (25 mL) was added at 5-15° C., allowed to rt, stirred for 2 h, quenched with ice-water, filtered, washed with water and dried under high vacuum to obtain 14 g (89%) 1-Nitro-4-(2,2,2-trifluoro-ethoxy)-benzene as yellow solid. Subsequently, a solution of 1-Nitro-4-(2,2,2-trifluoro-ethoxy)-benzene (50 g, 226.2 mmol) in methanol (400 mL) was purged with nitrogen and 10% Pd—C (4.6 g) was added under nitrogen. This was stirred at rt under hydrogen atmosphere (balloon pressure) for 24 h. The reaction mixture was filtered through a celite bed and washed with methanol and the filtrate was removed under reduced pressure and washed with hexane to get 37 g (87%) 4-(2,2,2-Trifluoro-ethoxy)-phenylamine as a brown liquid. LC-MS: 192.4 [M+1]+. To a solution of 4-(2,2,2-Trifluoro-ethoxy)-phenylamine (12 g, 62.82 mmol) in DCM (1000 mL) was added solid NaHCO$_3$ (52.77 g, 628.2 mmol). After 10 min, triphosgene (27.96 g, 94.24 mmol) dissolved in toluene (30 mL) was added to the reaction mixture under cooling at 10° C. and stirred for 10 min. The reaction mixture was filtered and the filtrate was concentrated, azeotroped twice with dry toluene to give 10 g 1-Isocyanato-4-(2,2,2-trifluoro-ethoxy)-benzene as yellow oily liquid which was used in the next step without further purification.

b) (2R,4S)-4-Hydroxy-1-[4-(2,2,2-trifluoro-ethoxy)-phenylcarbamoyl]-pyrrolidine-2-carboxylic acid methyl ester

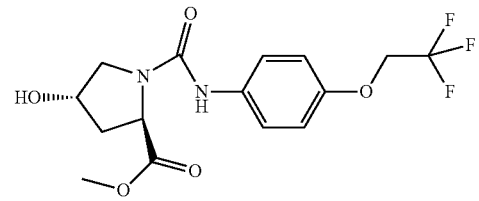 [SMILES: COC(=O)[C@H]1C[C@H](O)CN1C(=O)Nc1ccc(OCC(F)(F)F)cc1]

To a solution of (2R,4S)-4-Hydroxy-pyrrolidine-2-carboxylic acid methyl ester, hydrochloride (3 g, 16.57 mmol) in THF (15 mL) was added solid Na$_2$CO$_3$ (2.10 g, 19.88 mmol) and stirred for 15 min. To this mixture, freshly prepared 1-Isocyanato-4-(2,2,2-trifluoro-ethoxy)-benzene (4.3 g, 19.88 mmol) in THF (10 mL) was added and stirred for 2 h at room temperature. The reaction mixture was filtered and the filtrate was concentrated under reduced pressure. The residue was taken up in DCM and washed with water and brine, dried over Na$_2$SO$_4$ and concentrated to dryness. The residue was purified by column chromatography over silica (5% MeOH in DCM) to yield 2.7 g (50%) of the title compound as a white solid. LC-MS: 363.2 [M+1]+.

c) (2R,4S)-4-(tert-Butyl-diphenyl-silanyloxy)-1-[4-(2,2,2-trifluoro-ethoxy)-phenylcarbamoyl]-pyrrolidine-2-carboxylic acid methyl ester

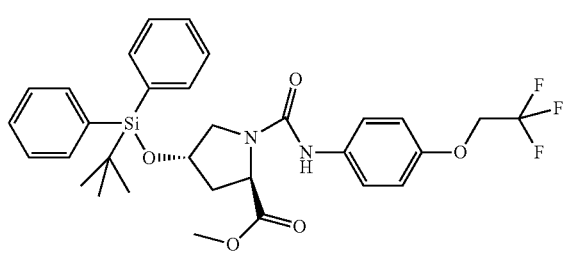 [SMILES: COC(=O)[C@H]1C[C@H](O[Si](c2ccccc2)(c2ccccc2)C(C)(C)C)CN1C(=O)Nc1ccc(OCC(F)(F)F)cc1]

To a solution of (2R,4S)-4-Hydroxy-1-[4-(2,2,2-trifluoro-ethoxy)-phenylcarbamoyl]-pyrrolidine-2-carboxylic acid methyl ester (3 g, 8.28 mmol) in DCM (15 ml), was added imidazole (1.69 g, 24.87 mmol) followed by TBDPS-Cl (3.5 g, 12.53 mmol) drop wise under cooling and stirred at room temperature for 2 h. Water was added, the organic layer separated and concentrated under reduced pressure. The residue was purified through column chromatography over silica (elution with 30% ethyl acetate in hexane) to yield 3.5 g (71%) of the TBDPS-protected urea as a colorless sticky liquid.

d) (2R,4S)-4-(tert-Butyl-diphenyl-silanyloxy)-2-hydroxymethyl-pyrrolidine-1-carboxylic acid [4-(2,2,2-trifluoro-ethoxy)-phenyl]-amide

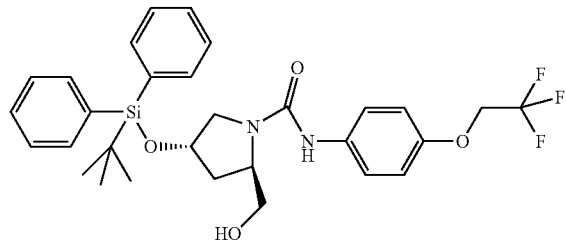 [SMILES: CC(C)(C)[Si](O[C@H]1C[C@H](CO)N(C(=O)Nc2ccc(OCC(F)(F)F)cc2)C1)(c1ccccc1)c1ccccc1]

To a solution of (2R,4S)-4-(tert-Butyl-diphenyl-silanyloxy)-1-[4-(2,2,2-trifluoro-ethoxy)-phenylcarbamoyl]-pyrrolidine-2-carboxylic acid methyl ester (5 g, 8.33 mmol) in THF (30 mL) was added LiBH$_4$ (2M in THF, 6.25 mL) at 0° C. and stirred for 2 h. The mixture was quenched with AcOH at 0° C. and diluted with DCM. The organic layer was washed with sat NaHCO$_3$ solution, dried over Na$_2$SO$_4$ and concentrated. The residue was purified through column chromatography over silica (elution with 40% ethyl acetate in hexane) to yield 4.3 g (91%) of the title compound as pale yellow sticky liquid. LC-MS: 573.6 [M+1]$^+$.

e) (6S,7aR)-6-(tert-Butyl-diphenyl-silanyloxy)-2-[4-(2,2,2-trifluoro-ethoxy)-phenyl]-hexahydro-pyrrolo[1,2-c]imidazol-3-one

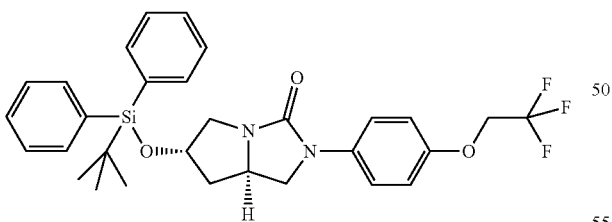

To a solution of (2R,4S)-4-(tert-Butyl-diphenyl-silanyloxy)-2-hydroxymethyl-pyrrolidine-1-carboxylic acid [4-(2,2,2-trifluoro-ethoxy)-phenyl]-amide (400 mg, 0.699 mmol) in DCM (5 mL) was added TEA (0.14 mL, 1.048 mmol) followed by mesylchloride (0.07 mL, 1.048 mmol) at 0° C. and stirred at room temperature for 12 h. DCM was added, the organic layer was washed with water and brine, dried over Na$_2$SO$_4$ and concentrated to dryness. 400 mg of the residue was taken up in THF (5 mL), t-BuOK (91 mg, 0.813 mmol) was added and the mixture was stirred for 1 h at room temperature. NH$_4$Cl aq. and DCM was added. The organic layer was washed with water and brine, dried over Na$_2$SO$_4$. The residue was purified through column chromatography over silica (elution with 10% ethyl acetate in hexane) to afford (6S,7aR)-6-(tert-Butyl-diphenyl-silanyloxy)-2-[4-(2,2,2-trifluoro-ethoxy)-phenyl]-hexahydro-pyrrolo[1,2-c]imidazol-3-one as an off white solid.

f) (6S,7aR)-6-Hydroxy-2-[4-(2,2,2-trifluoro-ethoxy)-phenyl]-hexahydro-pyrrolo[1,2-c]imidazol-3-one

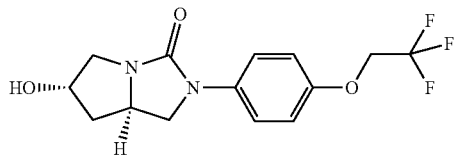 [SMILES: O=C1N(c2ccc(OCC(F)(F)F)cc2)C[C@H]2C[C@H](O)CN12]

To a solution of (6S,7aR)-6-(tert-Butyl-diphenyl-silanyloxy)-2-[4-(2,2,2-trifluoro-ethoxy)-phenyl]-hexahydro-pyrrolo[1,2-c]imidazol-3-one (250 mg, 0.451 mmol) in THF (3 mL) was added TBAF (1M in THF, 0.55 ml, 0.541 mmol) at 0° C. and stirred for 4 h at room temperature. The mixture was concentrated under reduced pressure and the residue was taken up with DCM. The organic layer was washed with water and brine, dried over Na$_2$SO$_4$ and concentrated. The residue was purified through column chromatography over silica (elution with 20% ethyl acetate in hexane) to afford 130 mg (90%) of the title compound. LC-MS: 317.4 [M+1]$^+$.

g) (6S,7aR)-6-(3-Methyl-butoxy)-2-[4-(2,2,2-trifluoro-ethoxy)-phenyl]-hexahydro-pyrrolo[1,2-c]imidazol-3-one To a solution of (6S,7aR)-6-Hydroxy-2-[4-(2,2,2-trifluoro-ethoxy)-phenyl]-hexahydro-pyrrolo[1,2-c]imidazol-3-one (100 mg, 0.316 mmol) in THF (3 mL) was added NaH (60% dispersion, 18.96 mg, 0.474 mmol) at room temperature and stirred for 30 min and then added 1-Bromo-3-methyl-butane (57.3 mg, 0.379 mmol) and left stirring for 12 h. The reaction mixture was quenched with NH$_4$Cl aq., DCM was added. The organic layer was separated, washed with water and brine, dried over Na$_2$SO$_4$ and concentrated. The residue was purified through column chromatography (elution with ethyl acetate in hexane) to afford 60 mg (49%) of the title compound. LC-MS: 386 [M+1]$^+$.

Example 34

(6S,7aR)-6-Isobutoxy-2-[4-(2,2,2-trifluoro-ethoxy)-phenyl]-hexahydro-pyrrolo[1,2-c]imidazol-3-one

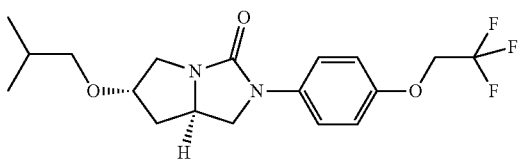 [SMILES: CC(C)CO[C@H]1C[C@@H]2CN(c3ccc(OCC(F)(F)F)cc3)C(=O)N2C1]

In analogy to the procedure described for the synthesis of (6S,7aR)-6-(3-Methyl-butoxy)-2-[4-(2,2,2-trifluoro-ethoxy)-phenyl]-hexahydro-pyrrolo[1,2-c]imidazol-3-one (example 33, step g) the title compound was prepared from (6S,7aR)-6-Hydroxy-2-[4-(2,2,2-trifluoro-ethoxy)-phenyl]-hexahydro-pyrrolo[1,2-c]imidazol-3-one and 1-Bromo-2-methyl-propane. LC-MS: 373 [M+1]+.

Example 35

2-Chloro-N-{(6S,7aR)-3-oxo-2-[4-(2,2,2-trifluoro-ethoxy)-phenyl]-hexahydro-pyrrolo[1,2-c]imidazol-6-yl}-benzenesulfonamide

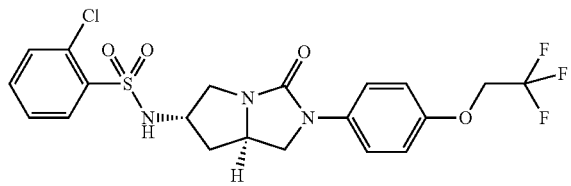 [SMILES: O=C1N(c2ccc(OCC(F)(F)F)cc2)C[C@H]2C[C@H](NS(=O)(=O)c3ccccc3Cl)CN12]

a) (6R,7aR)-6-Bromo-2-[4-(2,2,2-trifluoro-ethoxy)-phenyl]-hexahydro-pyrrolo[1,2-c]imidazol-3-one

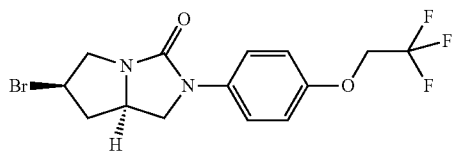 [SMILES: O=C1N(c2ccc(OCC(F)(F)F)cc2)C[C@H]2C[C@@H](Br)CN12]

To a solution of (6S,7aR)-6-Hydroxy-2-[4-(2,2,2-trifluoro-ethoxy)-phenyl]-hexahydro-pyrrolo[1,2-c]imidazol-3-one (example 33, step f) (900 mg, 2.848 mmol) in acetonitrile (10 ml) was added CBr$_4$ (2.24 g, 8.544 mmol) at room temperature and stirred for 10 min. PPh$_3$ (2.83 g, 8.544 mmol) was added and left stirring for 12 h at room temperature. The mixture was concentrated and the residue was purified through column chromatography over silica (elution with 10% ethyl acetate in hexane) to yield 850 mg (79%) of the title compound as white solid. LC-MS: 381.1 [M+1]+.

b) 2-Chloro-N-{(6S,7aR)-3-oxo-2-[4-(2,2,2-trifluoro-ethoxy)-phenyl]-hexahydro-pyrrolo[1,2-c]imidazol-6-yl}-benzenesulfonamide To a solution of (6R,7aR)-6-Bromo-2-[4-(2,2,2-trifluoro-ethoxy)-phenyl]-hexahydro-pyrrolo[1,2-c]imidazol-3-one (50 mg, 0.130 mmol) in DMF (3 mL) in a sealed tube, was added K$_2$CO$_3$ (27.3 mg, 0.197 mmol) and 2-Chloro-benzenesulfonamide (50.5 mg, 0.263 mmol) and heated to 80° C. for 12 h. All volatiles were removed under reduced pressure and the residue was extracted with ethyl acetate. The organic layer was separated, washed with water and brine, dried over Na$_2$SO$_4$ and concentrated. The residue was purified through biotage column chromatography (elution with 40% ethyl acetate in hexane) to afford 17 mg (26.5%) of the title compound as a white solid. LC-MS: 489 [M+1]+.

Example 36

(6R,7aR)-6-(3-Methyl-butoxy)-2-[4-(2,2,2-trifluoro-ethoxy)-phenyl]-hexahydro-pyrrolo[1,2-c]imidazol-3-one

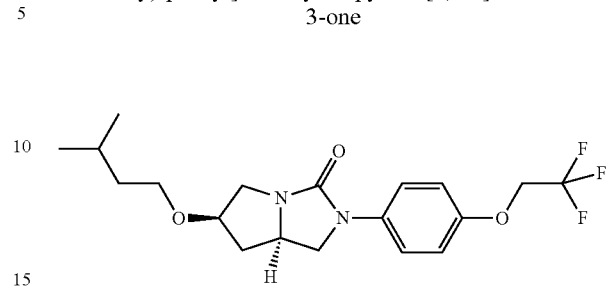

a) (6R,7aR)-6-Hydroxy-2-[4-(2,2,2-trifluoro-ethoxy)-phenyl]-hexahydro-pyrrolo[1,2-c]imidazol-3-one

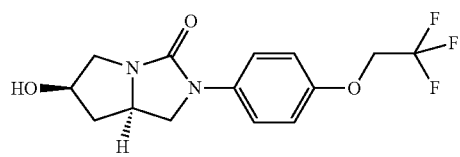 [SMILES: O=C1N(c2ccc(OCC(F)(F)F)cc2)C[C@H]2C[C@@H](O)CN12]

In analogy to the procedure described for the synthesis of (6S,7aR)-6-Hydroxy-2-[4-(2,2,2-trifluoro-ethoxy)-phenyl]-hexahydro-pyrrolo[1,2-c]imidazol-3-one (example 33, step f) the title compound was prepared through the same synthetic sequence starting from (2R,4R)-4-Hydroxy-pyrrolidine-2-carboxylic acid methyl ester, hydrochloride. LC-MS: 317.4 [M+1]+.

b) (6R,7aR)-6-(3-Methyl-butoxy)-2-[4-(2,2,2-trifluoro-ethoxy)-phenyl]-hexahydro-pyrrolo[1,2-c]imidazol-3-one In analogy to the procedure described for the synthesis of (6S,7aR)-6-(3-Methyl-butoxy)-2-[4-(2,2,2-trifluoro-ethoxy)-phenyl]-hexahydro-pyrrolo[1,2-c]imidazol-3-one (example 33) the title compound was prepared from (6R,7aR)-6-Hydroxy-2-[4-(2,2,2-trifluoro-ethoxy)-phenyl]-hexahydro-pyrrolo[1,2-c]imidazol-3-one and 1-Bromo-3-methyl-butane. LC-MS: 387 [M+1]+.

Example 37

2-Chloro-N-{(6R,7aR)-3-oxo-2-[4-(2,2,2-trifluoro-ethoxy)-phenyl]-hexahydro-pyrrolo[1,2-c]imidazol-6-yl}-benzenesulfonamide

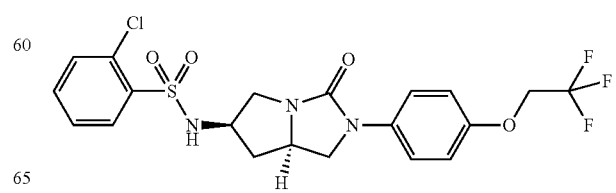

a) (6S,7aR)-6-Bromo-2-[4-(2,2,2-trifluoro-ethoxy)-phenyl]-hexahydro-pyrrolo[1,2-c]imidazol-3-one

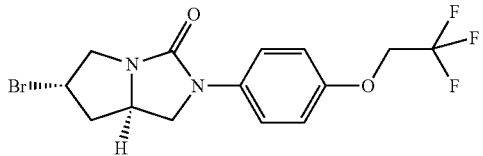 [SMILES: O=C1N(c2ccc(OCC(F)(F)F)cc2)C[C@H]2C[C@H](Br)CN12]

In analogy to the procedure described for the synthesis of (6R,7aR)-6-Bromo-2-[4-(2,2,2-trifluoro-ethoxy)-phenyl]-hexahydro-pyrrolo[1,2-c]imidazol-3-one (example 35, step a) the title compound was prepared from (6R,7aR)-6-Hydroxy-2-[4-(2,2,2-trifluoro-ethoxy)-phenyl]-hexahydro-pyrrolo[1,2-c]imidazol-3-one (example 36, step a). LC-MS: 379.4 [M+1]$^+$.

b) 2-Chloro-N-{(6R,7aR)-3-oxo-2-[4-(2,2,2-trifluoro-ethoxy)-phenyl]-hexahydro-pyrrolo[1,2-c]imidazol-6-yl}-benzenesulfonamide In analogy to the procedure described for the synthesis of 2-Chloro-N-{(6S,7aR)-3-oxo-2-[4-(2,2,2-trifluoro-ethoxy)-phenyl]-hexahydro-pyrrolo[1,2-c]imidazol-6-yl}-benzenesulfonamide (example 35) the title compound was prepared from (6S,7aR)-6-Bromo-2-[4-(2,2,2-trifluoro-ethoxy)-phenyl]-hexahydro-pyrrolo[1,2-c]imidazol-3-one and 2-Chloro-benzenesulfonamide. LC-MS: 489 [M+1]$^+$.

Example 38

(6S,7aS)-6-Butoxymethyl-6-hydroxy-2-[4-(2,2,2-trifluoro-ethoxy)-phenyl]-hexahydro-pyrrolo[1,2-c]imidazol-3-one

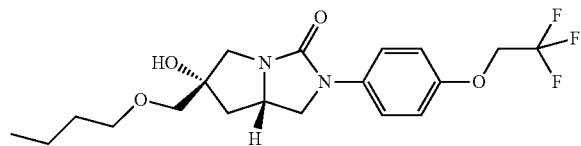 [SMILES: CCCCOC[C@]1(O)C[C@H]2CN(c3ccc(OCC(F)(F)F)cc3)C(=O)N2C1]

a) (S)-6-Hydroxy-2-[4-(2,2,2-trifluoro-ethoxy)-phenyl]-hexahydro-pyrrolo[1,2-c]imidazol-3-one

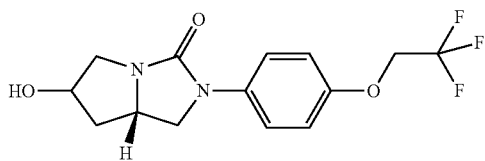 [SMILES: O=C1N(c2ccc(OCC(F)(F)F)cc2)C[C@@H]2CC(O)CN12]

In analogy to the procedure described for the synthesis of (6S,7aR)-6-Hydroxy-2-[4-(2,2,2-trifluoro-ethoxy)-phenyl]-hexahydro-pyrrolo[1,2-c]imidazol-3-one (example 33, step f) the title compound was prepared through the same synthetic sequence starting from (S)-4-Hydroxy-pyrrolidine-2-carboxylic acid methyl ester, hydrochloride. LC-MS: 317.4 [M+1]$^+$.

b) (S)-2-[4-(2,2,2-Trifluoro-ethoxy)-phenyl]-tetrahydro-pyrrolo[1,2-c]imidazole-3,6-dione

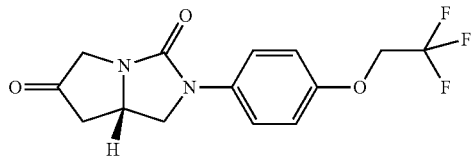 [SMILES: O=C1C[C@H]2CN(c3ccc(OCC(F)(F)F)cc3)C(=O)N2C1]

To the solution of (S)-6-Hydroxy-2-[4-(2,2,2-trifluoro-ethoxy)-phenyl]-hexahydro-pyrrolo[1,2-c]imidazol-3-one (1 g, 3.16 mmol) in dry DCM (20 mL) was added PDC (3.6 g, 9.48 mmol) portion wise under cooling. The reaction mixture was stirred at room temperature for 13 h. Then reaction mixture was filtered and washed with methanol, the filtrate was evaporated under reduced pressure. The residue was purified by column chromatography on silica gel (elution with 30% ethyl acetate in hexane) to yield 500 mg (50%) of the title compound as white solid. LC-MS: 315.4 [M+1]$^+$.

c) (2R,7a'S)-2'-[4-(2,2,2-trifluoroethoxy)phenyl]tetrahydro-3'H-spiro[oxirane-2,6'-pyrrolo[1,2-c]imidazol]-3'-one and (2S,7a'S)-2'-[4-(2,2,2-trifluoroethoxy)phenyl]tetrahydro-3'H-spiro[oxirane-2,6'-pyrrolo[1,2-c]imidazol]-3'-one

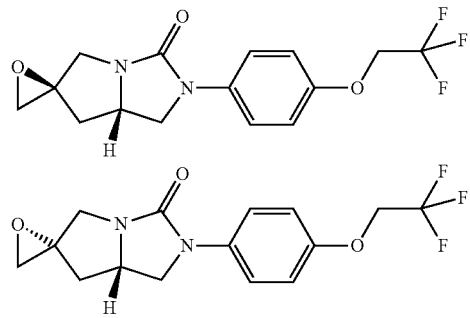

To a mixture of trimethyl sulfoxonium iodide (70 mg, 0.350 mmol) and NaH (20 mg, 0.477 mmol), was added dry DMSO (0.3 mL) drop wise at 0° C. and stirred for 30 min. (S)-2-[4-(2,2,2-Trifluoro-ethoxy)-phenyl]-tetrahydro-pyrrolo[1,2-c]imidazole-3,6-dione (100 mg, 0.318 mmol) dissolved in DMSO (0.6 mL) was added to this mixture and stirred at room temperature for 2 h. The reaction mixture was poured into brine and extracted with ethyl acetate. The organic layer was dried over Na$_2$SO$_4$ and concentrated. The residue was purified through column chromatography over silica (elution with 30% ethyl acetate in hexane) to obtain 20 mg of isomer (2R,7a'S)-2'-[4-(2,2,2-trifluoroethoxy)phenyl]tetrahydro-3'H-spiro[oxirane-2,6'-pyrrolo[1,2-c]imidazol]-3'-one (off white solid) LC-MS: 329.0 [M+1]$^+$ and 5 mg of isomer (2S,7a'S)-2'-[4-(2,2,2-trifluoroethoxy)phenyl]tetrahydro-3'H-spiro[oxirane-2,6'-pyrrolo[1,2-c]imidazol]-3'-one (off white solid) LC-MS: 329.0 [M+1]$^+$.

d) (6S,7aS)-6-Butoxymethyl-6-hydroxy-2-[4-(2,2,2-trifluoro-ethoxy)-phenyl]-hexahydro-pyrrolo[1,2-c]imidazol-3-one To a stirred solution of (2S,7a'S)-2'-[4-(2,2,2-trifluoroethoxy)phenyl]tetrahydro-3'H-spiro[oxirane-2,6'-pyrrolo[1,2-c]imidazol]-3'-one (40 mg, 0.121 mmol) in butanol (5 mL) was added NaH (60% in oil, 7.3 mg, 0.18 mmol) and heated to reflux for 12 h. The reaction mixture quenched with water and extracted with ethyl acetate. The organic layer was washed with water and brine, dried over $Na_2SO_4$ and concentrated. The residue purified by column chromatography on silica eluting with ethyl acetate/hexane to yield 12 mg (24%) of the title compound as white solid. LC-MS: 403.0 [M+1]$^+$.

Example 39

(6S,7aS)-6-Ethoxymethyl-6-hydroxy-2-[4-(2,2,2-trifluoro-ethoxy)-phenyl]-hexahydro-pyrrolo[1,2-c]imidazol-3-one

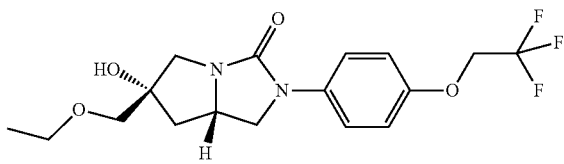 [SMILES: CCOC[C@]1(O)C[C@H]2CN(c3ccc(OCC(F)(F)F)cc3)C(=O)N2C1]

In analogy to the procedure described for the synthesis of (6S,7aS)-6-Butoxymethyl-6-hydroxy-2-[4-(2,2,2-trifluoro-ethoxy)-phenyl]-hexahydro-pyrrolo[1,2-c]imidazol-3-one (example 38) the title compound was prepared from (2S,7a'S)-2'-[4-(2,2,2-trifluoroethoxy)phenyl]tetrahydro-3'H-spiro[oxirane-2,6'-pyrrolo[1,2-c]imidazol]-3'-one and NaOEt (21% in ethanol) as off-white solid. LC-MS: 375.0 [M+1]$^+$.

Example 40

(6S,7aS)-6-Hydroxy-6-(2,2,2-trifluoro-ethoxymethyl)-2-[4-(2,2,2-trifluoro-ethoxy)-phenyl]-hexahydro-pyrrolo[1,2-c]imidazol-3-one

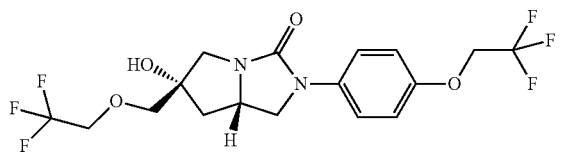 [SMILES: O=C1N(c2ccc(OCC(F)(F)F)cc2)C[C@@H]2C[C@@](O)(COCC(F)(F)F)CN12]

In analogy to the procedure described for the synthesis of (6S,7aS)-6-Butoxymethyl-6-hydroxy-2-[4-(2,2,2-trifluoro-ethoxy)-phenyl]-hexahydro-pyrrolo[1,2-c]imidazol-3-one (example 38) the title compound was prepared from (2S,7a'S)-2'-[4-(2,2,2-trifluoroethoxy)phenyl]tetrahydro-3'H-spiro[oxirane-2,6'-pyrrolo[1,2-c]imidazol]-3'-one and 2,2,2-Trifluoro-ethanol (deprotonated with NaH) as off-white solid after purification with column chromatography over silica elution with 50% ethyl acetate in hexane. LC-MS: 375.0 [M+1]$^+$.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound according to formula (I),

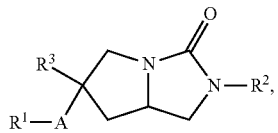

wherein

R$^1$ is selected from the group consisting of: alkyl, haloalkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, heteroaryl, substituted heteroaryl, heteroarylalkyl and substituted heteroarylalkyl; wherein said substituted phenyl, substituted phenylalkyl, substituted phenoxyalkyl, substituted heteroaryl and substituted heteroarylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl;

R$^2$ is phenyl substituted with one haloalkoxy;

R$^3$ is selected from the group consisting of: hydrogen, hydroxy and alkoxy, wherein, when R$^3$ is hydroxy or alkoxy, A is a bond;

R$^4$ is selected from the group consisting of: hydrogen, alkyl and cycloalkyl;

R$^5$ is selected from the group consisting of: hydrogen, alkyl and cycloalkyl; and A is selected from the group consisting of: —O—, —OC(O)—, —NR⁴C(O)O—, —NR⁴—, —C(O)NR⁴—, —NR⁴C(O)NR⁵—, —S(O)₂NR⁴—, —NR⁴S(O)NR⁵—, —NR⁴S(O)₂NR⁵—, —S—, —S(O)—, —S(O)₂— and a bond,
wherein, when A is a bond, R¹ is alkoxyalkyl or haloalkoxyalkyl;
or a pharmaceutically acceptable salt thereof.

2. A compound according to claim 1, wherein R¹ is selected from the group consisting of: alkyl, alkoxyalkyl, haloalkoxyalkyl, hydroxyalkyl, phenyl, substituted phenyl, phenylalkyl, substituted phenylalkyl, phenoxyalkyl, substituted phenoxyalkyl, pyridinyl, substituted pyridinyl, pyridinylalkyl and substituted pyridinylalkyl; wherein said substituted phenyl, substituted phenylalkyl, substituted phenoxyalkyl, substituted pyridinyl and substituted pyridinylalkyl are substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl and alkoxyhaloalkyl.

3. A compound according to claim 1, wherein R¹ is selected from the group consisting of: alkyl, alkoxyalkyl, haloalkoxyalkyl, hydroxyalkyl, substituted phenyl, phenylalkyl, substituted phenylalkyl, phenoxyalkyl and substituted pyridinyl; wherein said substituted phenyl, substituted phenylalkyl and substituted pyridinyl are substituted with one to three substituents independently selected from the group consisting of alkyl, halogen and hydroxy.

4. A compound according to claim 1, wherein R¹ is haloalkoxyalkyl or phenyl substituted with one halogen.

5. A compound according to claim 1, wherein R¹ is haloalkoxyalkyl.

6. A compound according to claim 1, wherein R¹ is 2,2,2-trifluoroethoxymethyl.

7. A compound according to claim 1, wherein R¹ is phenyl substituted with one halogen.

8. A compound according to claim 1, wherein R¹ is selected from the group consisting of: 2-chlorophenyl, 2-fluorophenyl, 3-fluorophenyl and 4-chlorophenyl.

9. A compound according to claim 1, wherein R² is phenyl substituted with one substituent selected from trifluoromethoxy and 2,2,2-trifluoroethoxy.

10. A compound according to claim 1, wherein R² is 4-trifluoromethoxyphenyl or 4-(2,2,2-trifluoroethoxy)phenyl.

11. A compound according to claim 1, wherein R² is 4-trifluoromethoxyphenyl.

12. A compound according to claim 1, wherein R³ is hydrogen or hydroxy, wherein, when R³ is hydroxy, A is a bond.

13. A compound according to claim 1, wherein R³ is hydrogen.

14. A compound according to claim 1, wherein R³ is hydroxy and A is a bond.

15. A compound according to claim 1, wherein R⁴ is hydrogen or alkyl.

16. A compound according to claim 1, wherein R⁴ is hydrogen.

17. A compound according to claim 1, wherein R⁴ is alkyl.

18. A compound according to claim 1, wherein R⁵ is hydrogen.

19. A compound according to claim 1, wherein A is selected from the group consisting of: —O—, —NR⁴C(O)O—, —C(O)NR⁴—, —NR⁴C(O)NR⁵—, —S(O)₂NR⁴—, —S(O)₂— and a bond, wherein, when A is a bond, R¹ is alkoxyalkyl or haloalkoxyalkyl.

20. A compound according to claim 1, wherein A is a bond and R¹ is alkoxyalkyl or haloalkoxyalkyl.

21. A compound according to claim 1, wherein R¹ and A together form R¹—O—, R¹—NR⁴C(O)O—, R¹—C(O)NR⁴—, R¹—NR⁴C(O)NR⁵—, R¹—S(O)₂NR⁴— or R¹—S(O)₂—.

22. A compound according to claim 1, wherein A is —S(O)₂NR⁴—.

23. A compound according to claim 1, wherein A is —O—.

24. A compound according to claim 1, wherein A is —C(O)NR⁴—.

25. A compound according to claim 1, wherein A is —NR⁴C(O)NR⁵—.

26. A compound according to claim 1 of formula (Ia)

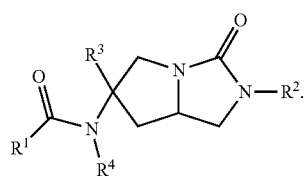

(Ia)

27. A compound according to claim 1 of formula (Ib)

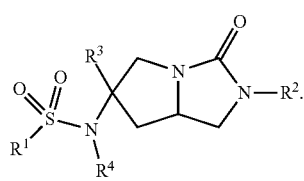

(Ib)

28. A compound according to claim 1, selected from the group consisting of:
2-Chloro-N-[(6R,7aS)-3-oxo-2-(4-trifluoromethoxy-phenyl)-hexahydro-pyrrolo[1,2-c]imidazol-6-yl]-benzamide;
2-Chloro-N-[(6R,7aS)-3-oxo-2-(4-trifluoromethoxy-phenyl)-hexahydro-pyrrolo[1,2-c]imidazol-6-yl]-benzenesulfonamide;
(6R,7aS)-6-(Toluene-4-sulfonyl)-2-(4-trifluoromethoxy-phenyl)-hexahydro-pyrrolo[1,2-c]imidazol-3-one;
(6R,7aS)-6-(3-Methyl-butane-1-sulfonyl)-2-(4-trifluoromethoxy-phenyl)-hexahydro-pyrrolo[1,2-c]imidazol-3-one;
(6R,7aS)-6-(4-Fluoro-benzenesulfonyl)-2-(4-trifluoromethoxy-phenyl)-hexahydro-pyrrolo[1,2-c]imidazol-3-one;
(6R,7aS)-6-(1-Phenyl-ethoxy)-2-(4-trifluoromethoxy-phenyl)-hexahydro-pyrrolo[1,2-c]imidazol-3-one;
Propyl-carbamic acid (6R,7aS)-3-oxo-2-(4-trifluoromethoxy-phenyl)-hexahydro-pyrrolo[1,2-c]imidazol-6-yl ester;
(4-Fluoro-benzyl)-carbamic acid (6R,7aS)-3-oxo-2-(4-trifluoromethoxy-phenyl)-hexahydro-pyrrolo[1,2-c]imidazol-6-yl ester;
N-[(6R,7aS)-3-Oxo-2-(4-trifluoromethoxy-phenyl)-hexahydro-pyrrolo[1,2-c]imidazol-6-yl]-C-phenyl-methanesulfonamide;
4-Methyl-N-[(6R,7aS)-3-oxo-2-(4-trifluoromethoxy-phenyl)-hexahydro-pyrrolo[1,2-c]imidazol-6-yl]-benzenesulfonamide;
and pharmaceutically acceptable salts thereof.

29. A compound according to claim 1, selected from the group consisting of:
- 2-Methyl-propane-1-sulfonic acid [(6R,7aS)-3-oxo-2-(4-trifluoromethoxy-phenyl)-hexahydro-pyrrolo[1,2-c]imidazol-6-yl]-amide;
- 3-Chloro-N-[(6R,7aS)-3-oxo-2-(4-trifluoromethoxy-phenyl)-hexahydro-pyrrolo[1,2-c]imidazol-6-yl]-benzenesulfonamide;
- 4-Chloro-N-[(6R,7aS)-3-oxo-2-(4-trifluoromethoxy-phenyl)-hexahydro-pyrrolo[1,2-c]imidazol-6-yl]-benzenesulfonamide;
- 2-Fluoro-N-[(6R,7aS)-3-oxo-2-(4-trifluoromethoxy-phenyl)-hexahydro-pyrrolo[1,2-c]imidazol-6-yl]-benzenesulfonamide;
- 2-Chloro-pyridine-3-sulfonic acid [(6R,7aS)-3-oxo-2-(4-trifluoromethoxy-phenyl)-hexahydro-pyrrolo[1,2-c]imidazol-6-yl]-amide;
- 2-Hydroxy-pyridine-3-sulfonic acid [(6R,7aS)-3-oxo-2-(4-trifluoromethoxy-phenyl)-hexahydro-pyrrolo[1,2-c]imidazol-6-yl]-amide;
- 1-Methyl-3-[(6R,7aS)-3-oxo-2-(4-trifluoromethoxy-phenyl)-hexahydro-pyrrolo[1,2-c]imidazol-6-yl]-1-propyl-urea;
- 1-(3-Fluoro-phenyl)-1-methyl-3-[(6R,7aS)-3-oxo-2-(4-trifluoromethoxy-phenyl)-hexahydro-pyrrolo[1,2-c]imidazol-6-yl]-urea;
- 3-Chloro-N-[(6R,7aS)-3-oxo-2-(4-trifluoromethoxy-phenyl)-hexahydro-pyrrolo[1,2-c]imidazol-6-yl]-benzamide;
- 4-Methyl-N-[(6S,7aS)-3-oxo-2-(4-trifluoromethoxy-phenyl)-hexahydro-pyrrolo[1,2-c]imidazol-6-yl]-benzenesulfonamide;

and pharmaceutically acceptable salts thereof.

30. A compound according to claim 1, selected from the group consisting of:
- 4-Chloro-N-[(6R,7aS)-3-oxo-2-(4-trifluoromethoxy-phenyl)-hexahydro-pyrrolo[1,2-c]imidazol-6-yl]-benzamide;
- 2-Fluoro-N-[(6R,7aS)-3-oxo-2-(4-trifluoromethoxy-phenyl)-hexahydro-pyrrolo[1,2-c]imidazol-6-yl]-benzamide;
- 4-Chloro-N-[(6S,7aS)-3-oxo-2-(4-trifluoromethoxy-phenyl)-hexahydro-pyrrolo[1,2-c]imidazol-6-yl]-benzenesulfonamide;
- 3,3-Dimethyl-N-[(6R,7aS)-3-oxo-2-(4-trifluoromethoxy-phenyl)-hexahydro-pyrrolo[1,2-c]imidazol-6-yl]-butyramide;
- 2-Chloro-pyridine-3-sulfonic acid [(6S,7aS)-3-oxo-2-(4-trifluoromethoxy-phenyl)-hexahydro-pyrrolo[1,2-c]imidazol-6-yl]-amide;
- N-[(6R,7aS)-3-Oxo-2-(4-trifluoromethoxy-phenyl)-hexahydro-pyrrolo[1,2-c]imidazol-6-yl]-2-phenoxy-acetamide;
- 2-tert-Butoxy-N-[(6R,7aS)-3-oxo-2-(4-trifluoromethoxy-phenyl)-hexahydro-pyrrolo[1,2-c]imidazol-6-yl]-acetamide;
- 3-Chloro-N-[(6S,7aS)-3-oxo-2-(4-trifluoromethoxy-phenyl)-hexahydro-pyrrolo[1,2-c]imidazol-6-yl]-benzenesulfonamide;
- 2-Fluoro-N-[(6S,7aS)-3-oxo-2-(4-trifluoromethoxy-phenyl)-hexahydro-pyrrolo[1,2-c]imidazol-6-yl]-benzenesulfonamide;
- 2-Methyl-propane-1-sulfonic acid [(6S,7aS)-3-oxo-2-(4-trifluoromethoxy-phenyl)-hexahydro-pyrrolo[1,2-c]imidazol-6-yl]-amide;

and pharmaceutically acceptable salts thereof.

31. A compound according to claim 1, selected from the group consisting of:
- N-[(6S,7aS)-3-Oxo-2-(4-trifluoromethoxy-phenyl)-hexahydro-pyrrolo[1,2-c]imidazol-6-yl]-C-phenyl-methanesulfonamide;
- (6R,7aS)-6-(2-Hydroxy-pentyloxy)-2-(4-trifluoromethoxy-phenyl)-hexahydro-pyrrolo[1,2-c]imidazol-3-one;
- (6S,7aR)-6-(3-Methyl-butoxy)-2-[4-(2,2,2-trifluoro-ethoxy)-phenyl]-hexahydro-pyrrolo[1,2-c]imidazol-3-one;
- (6S,7aR)-6-Isobutoxy-2-[4-(2,2,2-trifluoro-ethoxy)-phenyl]-hexahydro-pyrrolo[1,2-c]imidazol-3-one;
- 2-Chloro-N-{(6S,7aR)-3-oxo-2-[4-(2,2,2-trifluoro-ethoxy)-phenyl]-hexahydro-pyrrolo[1,2-c]imidazol-6-yl}-benzenesulfonamide;
- (6R,7aR)-6-(3-Methyl-butoxy)-2-[4-(2,2,2-trifluoro-ethoxy)-phenyl]-hexahydro-pyrrolo[1,2-c]imidazol-3-one;
- 2-Chloro-N-{(6R,7aR)-3-oxo-2-[4-(2,2,2-trifluoro-ethoxy)-phenyl]-hexahydro-pyrrolo[1,2-c]imidazol-6-yl}-benzenesulfonamide;
- (6S,7aS)-6-Butoxymethyl-6-hydroxy-2-[4-(2,2,2-trifluoro-ethoxy)-phenyl]-hexahydro-pyrrolo[1,2-c]imidazol-3-one;
- (6S,7aS)-6-Ethoxymethyl-6-hydroxy-2-[4-(2,2,2-trifluoro-ethoxy)-phenyl]-hexahydro-pyrrolo[1,2-c]imidazol-3-one;
- (6S,7aS)-6-Hydroxy-6-(2,2,2-trifluoro-ethoxymethyl)-2-[4-(2,2,2-trifluoro-ethoxy)-phenyl]-hexahydro-pyrrolo[1,2-c]imidazol-3-one;

and pharmaceutically acceptable salts thereof.

32. A compound according to claim 1, selected from
- 2-Chloro-N-[(6R,7aS)-3-oxo-2-(4-trifluoromethoxy-phenyl)-hexahydro-pyrrolo[1,2-c]imidazol-6-yl]-benzenesulfonamide;
- 2-Fluoro-N-[(6R,7aS)-3-oxo-2-(4-trifluoromethoxy-phenyl)-hexahydro-pyrrolo[1,2-c]imidazol-6-yl]-benzenesulfonamide;
- 1-(3-Fluoro-phenyl)-1-methyl-3-[(6R,7aS)-3-oxo-2-(4-trifluoromethoxy-phenyl)-hexahydro-pyrrolo[1,2-c]imidazol-6-yl]-urea;
- 4-Chloro-N-[(6R,7aS)-3-oxo-2-(4-trifluoromethoxy-phenyl)-hexahydro-pyrrolo[1,2-c]imidazol-6-yl]-benzamide;
- (6S,7aS)-6-Hydroxy-6-(2,2,2-trifluoro-ethoxymethyl)-2-[4-(2,2,2-trifluoro-ethoxy)-phenyl]-hexahydro-pyrrolo[1,2-c]imidazol-3-one;

and pharmaceutically acceptable salts thereof.

33. A pharmaceutical composition comprising a compound according to claim 1 and a therapeutically inert carrier.

* * * * *